US009645097B2

(12) United States Patent
Nicolaides et al.

(10) Patent No.: US 9,645,097 B2
(45) Date of Patent: May 9, 2017

(54) IN-LINE WAFER EDGE INSPECTION, WAFER PRE-ALIGNMENT, AND WAFER CLEANING

(71) Applicant: KLA-Tencor Corporation, Milpitas, CA (US)

(72) Inventors: Lena Nicolaides, Castro Valley, CA (US); Ben-ming Benjamin Tsai, Saratoga, CA (US); Prashant A. Aji, San Jose, CA (US); Michael Gasvoda, Los Gatos, CA (US); Stanley E. Stokowski, Danville, CA (US); Guoheng Zhao, Palo Alto, CA (US); Youxian Wen, Fremont, CA (US); Mohan Mahadevan, Santa Clara, CA (US); Paul D. Horn, Milpitas, CA (US); Wolfgang Vollrath, Burbach (DE); Isabella T. Lewis, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/741,866

(22) Filed: Jun. 17, 2015

(65) Prior Publication Data
US 2015/0370175 A1    Dec. 24, 2015

Related U.S. Application Data

(60) Provisional application No. 62/014,986, filed on Jun. 20, 2014.

(51) Int. Cl.
*G03B 27/52* (2006.01)
*G03B 27/32* (2006.01)
(Continued)

(52) U.S. Cl.
CPC ....... *G01N 21/9503* (2013.01); *G03F 7/7085* (2013.01); *H01L 22/12* (2013.01); *G01N 2201/06113* (2013.01)

(58) Field of Classification Search
CPC ........ G01N 1/00; G03F 7/70066; G03F 7/20; G03F 7/7085
(Continued)

(56) References Cited

U.S. PATENT DOCUMENTS

| 5,440,391 A | 8/1995 | Smeyers et al. |
|---|---|---|
| 5,511,934 A | 4/1996 | Bacchi et al. |

(Continued)

FOREIGN PATENT DOCUMENTS

| AT | 531075 T | 11/2011 |
|---|---|---|
| CN | 101292263 A | 10/2008 |

(Continued)

OTHER PUBLICATIONS

Matthias, T , "Thin wafer processing—yield enhancement through integrated metrology", Electronics Packaging Technology Conference (EPTC), IEEE 13th, Dec. 2011, pp. 113-116.

(Continued)

*Primary Examiner* — Hung Henry Nguyen
(74) *Attorney, Agent, or Firm* — Kwan & Olynick LLP

(57) ABSTRACT

Disclosed are methods and apparatus for inspecting and processing semiconductor wafers. The system includes an edge detection system for receiving each wafer that is to undergo a photolithography process. The edge detection system comprises an illumination channel for directing one or more illumination beams towards a side, top, and bottom edge portion that are within a border region of the wafer. The edge detection system also includes a collection module for collecting and sensing output radiation that is scattered or reflected from the edge portion of the wafer and an analyzer module for locating defects in the edge portion and determining whether each wafer is within specification based on the sensed output radiation for such wafer. The photolithography system is configured for receiving from the edge detection system each wafer that has been found to be within (Continued)

specification. The edge detection system is coupled in-line with the photolithography system.

21 Claims, 19 Drawing Sheets

(51) Int. Cl.
  *G01N 21/95* (2006.01)
  *G03F 7/20* (2006.01)
  *H01L 21/66* (2006.01)
(58) Field of Classification Search
  USPC ............ 355/30, 53, 67, 77; 356/237.1–237.4
  See application file for complete search history.

(56) References Cited

U.S. PATENT DOCUMENTS

| | | | |
|---|---|---|---|
| 5,957,618 A | 9/1999 | Sims et al. | |
| 6,208,411 B1 | 3/2001 | Vaez-iravani | |
| 6,248,988 B1 | 6/2001 | Krantz | |
| 6,324,298 B1 | 11/2001 | O'dell et al. | |
| 6,552,803 B1 | 4/2003 | Wang et al. | |
| 6,657,216 B1 | 12/2003 | Poris | |
| 6,707,608 B1 | 3/2004 | Arieli et al. | |
| 6,745,637 B2 | 6/2004 | Tegeder et al. | |
| 6,773,935 B2 | 8/2004 | Watkins et al. | |
| 6,778,282 B1 | 8/2004 | Smets et al. | |
| 6,954,267 B2 | 10/2005 | Abraham et al. | |
| 6,970,238 B2 | 11/2005 | Gerhard et al. | |
| 7,012,631 B2 | 3/2006 | Vodanovic | |
| 7,019,841 B2 | 3/2006 | Mathur | |
| 7,102,743 B2 | 9/2006 | Tsuji et al. | |
| 7,130,039 B2 | 10/2006 | Vaez-iravani et al. | |
| 7,142,300 B2 | 11/2006 | Rosengaus | |
| 7,149,341 B2 | 12/2006 | Hayashi et al. | |
| 7,158,235 B2 | 1/2007 | Mathur | |
| 7,197,178 B2 | 3/2007 | Simpkins | |
| 7,220,034 B2 | 5/2007 | Li | |
| 7,222,720 B2 | 5/2007 | Truyens | |
| 7,231,081 B2 | 6/2007 | Snow et al. | |
| 7,268,867 B2 | 9/2007 | Vollrath et al. | |
| 7,280,197 B1 | 10/2007 | Rosengaus | |
| 7,280,200 B2 | 10/2007 | Plemmons | |
| 7,326,929 B2 | 2/2008 | Chou | |
| 7,327,470 B2 | 2/2008 | Arieli et al. | |
| 7,359,068 B2 | 4/2008 | Yonescu | |
| 7,361,921 B2 | 4/2008 | Gerhard | |
| 7,382,450 B2 | 6/2008 | Heiden | |
| 7,397,553 B1 | 7/2008 | Mehanian et al. | |
| 7,433,034 B1 | 10/2008 | Huang | |
| 7,446,868 B1 | 11/2008 | Higgs et al. | |
| 7,477,370 B2 | 1/2009 | Michelsson et al. | |
| 7,477,401 B2 | 1/2009 | Marx et al. | |
| 7,489,394 B2 | 2/2009 | Wienecke et al. | |
| 7,508,504 B2 | 3/2009 | Jin et al. | |
| 7,511,293 B2 | 3/2009 | Raymond et al. | |
| 7,589,834 B2 | 9/2009 | Higgs | |
| 7,593,565 B2 | 9/2009 | Reich et al. | |
| 7,599,545 B2 | 10/2009 | Shibata et al. | |
| 7,616,804 B2 | 11/2009 | Pai et al. | |
| 7,656,519 B2 | 2/2010 | Meeks et al. | |
| 7,724,358 B2 | 5/2010 | Vaughnn | |
| 7,728,965 B2 | 6/2010 | Haller et al. | |
| 7,738,113 B1 | 6/2010 | Marx et al. | |
| 7,804,641 B2 | 9/2010 | Hammond et al. | |
| 7,813,541 B2 | 10/2010 | Sali et al. | |
| 7,835,566 B2 | 11/2010 | Reich et al. | |
| RE42,481 E | 6/2011 | Wang et al. | |
| 7,960,981 B2 | 6/2011 | Strom et al. | |
| 7,968,859 B2 | 6/2011 | Young et al. | |
| 8,045,788 B2 | 10/2011 | Watkins et al. | |
| 8,089,622 B2 | 1/2012 | Birkner et al. | |
| 8,175,372 B2 | 5/2012 | Pai et al. | |
| 8,194,301 B2 | 6/2012 | Zhao et al. | |
| 8,289,509 B2 | 10/2012 | Wenz | |
| 8,312,772 B2 | 11/2012 | Tas et al. | |
| 8,339,594 B2 | 12/2012 | Sakamoto | |
| 8,358,831 B2 | 1/2013 | Doe | |
| 8,380,472 B2 | 2/2013 | Wang et al. | |
| 8,395,783 B2 | 3/2013 | Donaher et al. | |
| 8,426,223 B2 | 4/2013 | Voges et al. | |
| 8,428,393 B2 | 4/2013 | Kraft | |
| 8,492,178 B2 | 7/2013 | Carlson et al. | |
| 2003/0196343 A1 | 10/2003 | Abraham et al. | |
| 2004/0051810 A1 | 3/2004 | Vodanovic | |
| 2004/0085549 A1 | 5/2004 | Smets et al. | |
| 2004/0169869 A1* | 9/2004 | Shin ................. G01B 21/9501 356/635 |
| 2004/0207836 A1 | 10/2004 | Chhibber et al. | |
| 2004/0233403 A1 | 11/2004 | Gerhard et al. | |
| 2005/0007603 A1 | 1/2005 | Arieli et al. | |
| 2005/0030528 A1 | 2/2005 | Geffen et al. | |
| 2006/0013471 A1 | 1/2006 | Flieswasser et al. | |
| 2006/0087660 A1 | 4/2006 | Zabolitzky et al. | |
| 2006/0213537 A1 | 9/2006 | Atalla | |
| 2006/0233433 A1 | 10/2006 | Flieswasser et al. | |
| 2006/0249965 A1 | 11/2006 | Gerhard et al. | |
| 2007/0057164 A1 | 3/2007 | Vaughnn et al. | |
| 2007/0077136 A1 | 4/2007 | Schenck | |
| 2007/0247618 A1 | 10/2007 | Graf et al. | |
| 2007/0273891 A1 | 11/2007 | Gerhard et al. | |
| 2008/0013089 A1 | 1/2008 | Ishii et al. | |
| 2008/0088851 A1 | 4/2008 | Arieli et al. | |
| 2008/0124489 A1 | 5/2008 | Yamamoto et al. | |
| 2008/0281548 A1 | 11/2008 | Algranati et al. | |
| 2008/0309927 A1* | 12/2008 | Grueneberg ........ G01N 21/9503 356/237.1 |
| 2009/0059215 A1 | 3/2009 | Mehanian et al. | |
| 2009/0079987 A1 | 3/2009 | Ben-Ezra et al. | |
| 2009/0116726 A1 | 5/2009 | Postolov et al. | |
| 2009/0161094 A1 | 6/2009 | Watkins | |
| 2010/0053603 A1* | 3/2010 | Sakaguchi ............. G01B 11/30 356/237.4 |
| 2010/0093910 A1 | 4/2010 | Halahmi et al. | |
| 2010/0194406 A1 | 8/2010 | Corulli et al. | |
| 2010/0239157 A1 | 9/2010 | O'dell et al. | |
| 2010/0245566 A1 | 9/2010 | Lev et al. | |
| 2010/0277717 A1 | 11/2010 | Stern et al. | |
| 2010/0282956 A1* | 11/2010 | Kimba ..................... H01J 37/28 250/252.1 |
| 2010/0305897 A1 | 12/2010 | Strom | |
| 2010/0321056 A1 | 12/2010 | Strom et al. | |
| 2011/0032534 A1 | 2/2011 | Malinovich et al. | |
| 2011/0037492 A1 | 2/2011 | Seubert et al. | |
| 2011/0085725 A1 | 4/2011 | Pai et al. | |
| 2011/0089965 A1 | 4/2011 | Endres et al. | |
| 2011/0094945 A1 | 4/2011 | Cohen et al. | |
| 2011/0102574 A1 | 5/2011 | Cohen | |
| 2011/0102771 A1 | 5/2011 | Shapirov | |
| 2011/0115903 A1 | 5/2011 | Shalem et al. | |
| 2011/0128371 A1 | 6/2011 | Gastaldo et al. | |
| 2011/0141267 A1 | 6/2011 | Lev et al. | |
| 2011/0141594 A1 | 6/2011 | Vaughn et al. | |
| 2011/0149275 A1 | 6/2011 | Nakano et al. | |
| 2011/0154764 A1 | 6/2011 | Wang et al. | |
| 2011/0164129 A1 | 7/2011 | Postolov et al. | |
| 2011/0164806 A1 | 7/2011 | Peleg et al. | |
| 2011/0190429 A1 | 8/2011 | Muhammad et al. | |
| 2011/0199480 A1* | 8/2011 | Lev ..................... G01N 21/9503 348/126 |
| 2011/0199764 A1 | 8/2011 | Shapirov | |
| 2011/0263049 A1 | 10/2011 | Voges et al. | |
| 2011/0268348 A1 | 11/2011 | Vaughnn | |
| 2012/0026489 A1 | 2/2012 | Zhao et al. | |
| 2012/0086796 A1 | 4/2012 | Lewis et al. | |
| 2013/0100441 A1 | 4/2013 | Tagawa et al. | |
| 2014/0253910 A1 | 9/2014 | Lewis | |

FOREIGN PATENT DOCUMENTS

| | | |
|---|---|---|
| CN | 101355694 A | 1/2009 |
| CN | 201207094 Y | 3/2009 |

(56) References Cited

FOREIGN PATENT DOCUMENTS

| | | |
|---|---|---|
| CN | 201207118 Y | 3/2009 |
| CN | 201210191 Y | 3/2009 |
| CN | 101430362 A | 5/2009 |
| CN | 101714180 A | 5/2010 |
| CN | 201765193 U | 3/2011 |
| DE | 102005014595 A1 | 10/2006 |
| DE | 102005014596 B3 | 1/2007 |
| EP | 1972887 A1 | 9/2008 |
| EP | 1466137 B1 | 4/2010 |
| EP | 2367200 A2 | 9/2011 |
| EP | 1112550 B1 | 10/2011 |
| IL | 105765 A | 9/1998 |
| IL | 162650 A | 9/2014 |
| JP | 2010002216 A | 1/2010 |
| KR | 20080056150 A | 6/2008 |
| KR | 1020090008463 | 1/2009 |
| KR | 20110082476 A | 7/2011 |
| TW | I275335 B | 3/2007 |
| TW | 200802630 A | 1/2008 |
| TW | 200802666 A | 1/2008 |
| TW | 200802670 A | 1/2008 |
| TW | 200804799 A | 1/2008 |
| TW | 200811414 A | 3/2008 |
| TW | 200813411 A | 3/2008 |
| TW | 200820364 A | 5/2008 |
| TW | 200821571 A | 5/2008 |
| TW | 200825433 A | 6/2008 |
| TW | 20080065584 A | 7/2008 |
| TW | 200839916 A | 10/2008 |
| TW | 200842399 A | 11/2008 |
| TW | 200844428 A | 11/2008 |
| TW | 200845259 A | 11/2008 |
| TW | 200848338 A | 12/2008 |
| TW | 200900678 A | 1/2009 |
| TW | 200902964 A | 1/2009 |
| TW | 200909326 A | 3/2009 |
| TW | 200910515 A | 3/2009 |
| TW | 200912292 A | 3/2009 |
| TW | 200912804 A | 3/2009 |
| TW | 200913822 A | 3/2009 |
| TW | 200916763 A | 4/2009 |
| TW | 200919612 A | 5/2009 |
| TW | 200920095 A | 5/2009 |
| TW | 200921037 A | 5/2009 |
| TW | 200935045 A | 8/2009 |
| TW | 200938766 A | 9/2009 |
| TW | 201000888 A | 1/2010 |
| TW | 201009326 A | 3/2010 |
| TW | 201018331 A | 5/2010 |
| TW | 201029084 A | 8/2010 |
| TW | 201101400 A | 1/2011 |
| TW | 201108125 A | 3/2011 |
| TW | 201109677 A | 3/2011 |
| TW | 201115667 A | 4/2011 |
| WO | WO02071046 A1 | 9/2002 |
| WO | 2005079154 A2 | 9/2005 |
| WO | 2005104658 A2 | 11/2005 |
| WO | 2006006150 A2 | 1/2006 |
| WO | 2006013563 A2 | 2/2006 |
| WO | 2007023487 A2 | 3/2007 |
| WO | 2007023500 A2 | 3/2007 |
| WO | 2007023501 A2 | 3/2007 |
| WO | WO2007023500 A2 | 3/2007 |
| WO | 2008007363 A2 | 1/2008 |
| WO | 2008015677 A2 | 2/2008 |
| WO | 2008053490 A2 | 5/2008 |
| WO | 2008090559 A1 | 7/2008 |
| WO | 2008090563 A2 | 7/2008 |
| WO | 2008102338 A1 | 8/2008 |
| WO | 2008102339 A1 | 8/2008 |
| WO | 2008152648 A2 | 12/2008 |
| WO | 2009010983 A2 | 1/2009 |
| WO | 2009024970 A2 | 2/2009 |
| WO | 2009024978 A2 | 2/2009 |
| WO | 2009047641 A2 | 4/2009 |
| WO | 2010061388 A1 | 6/2010 |
| WO | 2011004365 A1 | 1/2011 |
| WO | 2011044473 A1 | 4/2011 |
| WO | 2011060401 A1 | 5/2011 |

OTHER PUBLICATIONS

"U.S. Appl. No. 14/731,861, Notice of Allowance mailed Feb. 13, 2017", 7 pages.

"International Application Serial No. PCT/US2015/036820, Search Report mailed Sep. 30, 2015", 3 pages.

* cited by examiner

IN-LINE WAFER EDGE INSPECTION, WAFER PRE-ALIGNMENT, AND WAFER CLEANING

CROSS-REFERENCE TO RELATED APPLICATION

This application claims priority of U.S. Provisional Patent Application No. 62/014,986, entitled "Method for In-Line Semiconductor Wafer Edge Inspection, Simultaneous Pre-Alignment, and Wafer Cleaning", and filed 20 Jun. 2014 by Lena Nicolaides et al., which application is herein incorporated by reference in its entirety for all purposes.

TECHNICAL FIELD OF THE INVENTION

The invention generally relates to a field of wafer inspection and imaging. More particularly the present invention relates to apparatus and techniques for inspecting and imaging a rounded wafer edge.

BACKGROUND

Generally, the industry of semiconductor manufacturing involves highly complex techniques for fabricating integrating circuits using semiconductor materials which are layered and patterned onto a substrate, such as silicon. Due to the large scale of circuit integration and the decreasing size of semiconductor devices, the fabricated devices have become increasingly sensitive to defects. That is, defects which cause faults in the device are becoming increasingly smaller. The device can generally be required to be fault free prior to shipment to the end users or customers.

Various inspection systems are used within the semiconductor industry to detect defects on a semiconductor reticle or wafer. One type of inspection tool is an optical inspection system. In optical inspection systems, one or more radiation beams are directed towards the semiconductor wafer and a reflected and/or scattered beam is then detected. The detected beam may then be used to generate a detected electrical signal or an image, and such signal or image is then analyzed to determine whether defects are present on the wafer.

In a specific inspection application, the side of a wafer is imaged to obtain an image of the edge region of such wafer. There is a continuing need for improved inspection techniques and apparatus for imaging such edge regions.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a system for inspecting and processing semiconductor wafers is disclosed. The system comprises an edge detection system for receiving each wafer that is to undergo a photolithography process in a photolithography system prior to the photolithography process being performed on such wafer. This edge detection system comprises at least one illumination channel for directing one or more illumination beams towards an edge portion of the wafer, and such edge portion includes at least one side and a top, and bottom that are within a border region of the wafer. The edge detection system also has at least one collection module for collecting and sensing output radiation that is scattered or reflected from the edge portion of the wafer in response to the one or more illumination beams and an analyzer module for locating defects in the edge portion and determining whether each wafer is within specification based on the sensed output radiation for such wafer. The overall system further comprises a photolithography system for receiving from the edge detection system each wafer that has been found to be within specification, and the edge detection system is coupled in-line with the photolithography system.

In a specific implementation, the analyzer module of the edge detection system is further configured to determine an alignment position of each wafer, and such alignment position is received from the edge detection system by the photolithography system for alignment of such wafer during the photolithography process. In another example, the edge detection system is arranged to receive each wafer immediately prior to such wafer being processed by the photolithography system. In yet another embodiment, the at least one illumination channel includes a diffractive optical element for generating a plurality of illumination beams that are directed simultaneously onto the edge portion. In a further aspect, the edge detection system further includes at least one positioning mechanism for rotating each wafer under the illumination channel so that the plurality of illumination beams are scanned over the entire circumference of the edge portion of such wafer and for rotating the edge detection system over the top, bottom, and at least one side of the edge portion.

In another embodiment, the at least one collection module includes a darkfield channel for receiving output radiation scattered from each wafer and a brightfield channel for receiving output radiation reflected from each wafer. In a specific implementation, the at least one illumination channel includes a deflector mechanism for scanning the at least one illumination beam across the edge portion of each wafer. In another aspect, the at least one illumination channel and at least one collection channel are in the form of an edge inspector for inspecting the at least one side of the edge portion of each wafer and a top camera and a bottom camera for inspecting the top and bottom, respectively, of the edge portion of each wafer simultaneously during inspection of the at least one side. In another example, the at least one illumination channel and at least one collection channel are in the form of multiple cameras configured to simultaneously inspect the at least one side, top, and bottom of the edge portion of each wafer. In a further aspect, the cameras are arranged to be offset from each other along the at least one side, top, and bottom of the edge portion of each wafer.

In another implementation, the at least one illumination channel and at least one collection channel of the edge detection system comprise a curved diffuser having an internal surface for positioning towards the edge portion of each wafer and an external surface opposite the internal surface, a plurality of light sources for generating a plurality of illumination beams adjacent to a plurality of positions on the external surface of the diffuser so that the diffuser outputs uniform light over the edge portion of each sample at a plurality of incident angles, and a sensor for receiving output radiation scattered from the edge portion of each wafer in response to the incident light and generating a detected signal. The light sources, diffuser, and sensor are integrated into a compact format.

In another embodiment, the illumination channel is configured to provide bright field illumination and/or dark field illumination. In another aspect, the at least one collection channel is in the form of a fiber bundle having a plurality of first ends positioned so as to receive the output radiation from the at least one side, top, and bottom of the edge portion and a plurality of second opposite ends to output the received output radiation into a line-scan camera or time delay integration (TDI) camera. In yet another example, the at least one collection channel is in the form of a plurality of optical elements positioned so as to receive and direct the output radiation simultaneously from the at least one side, top, and bottom of the edge portion into a line-scan camera or time delay integration (TDI) camera. In another embodiment, the at least one illumination channel and at least one collection channel of the edge detection system comprise a plurality of blue-ray devices arranged over the edge portion of each wafer.

In an alternative embodiment, the invention pertains to a method of inspecting an edge portion of wafers which are to undergo a photolithography process in a photolithography system. The method comprises (i) for each wafer that is to undergo a photolithography process in the photolithography system, receiving the wafer into an edge detection system prior to the photolithography process being performed on such wafer, (ii) by the edge detection system, inspecting an edge portion of each wafer for defects to determine whether the wafer is within specification, wherein such edge portion includes at least one side and a top, and bottom that are within a border region of the wafer, and (iii) for each wafer that the edge detection system determines to be within specification, outputting the wafer from the edge detection system to the lithography system. The edge detection system is in-line with the photolithography system.

In a further aspect, the method includes tracking defects of a particular wafer that are found to be within specification during or after such particular wafer undergoes a photolithography process. In a specific embodiment, the edge detection system inspects wafers at a rate that is equal to or faster than a processing rate of the lithography system. In another aspect, the edge portion of each wafer is inspected with a plurality of simultaneous scanning spots that are rotated around the circumference of the wafer and stepped across the entire top and bottom and at least one side of the edge portion of the wafer. In a further aspect, the method includes (i) by the edge detection system, determining an alignment position of each wafer and (ii) receiving such alignment position for each wafer from the edge detection system into the photolithography system, which uses the received alignment positions for alignment of such wafer during the photolithography process. In a further aspect, the method includes cleaning each wafer that is determined to be out of specification and to be cleanable prior to sending the wafer to the photolithography system, and the cleaning is performed in an internal cleaning system that is in-line with the edge detection and photolithography system.

These and other aspects of the invention are described further below with reference to the figures.

DETAILED DESCRIPTION OF EXAMPLE EMBODIMENTS

Figure 1A:
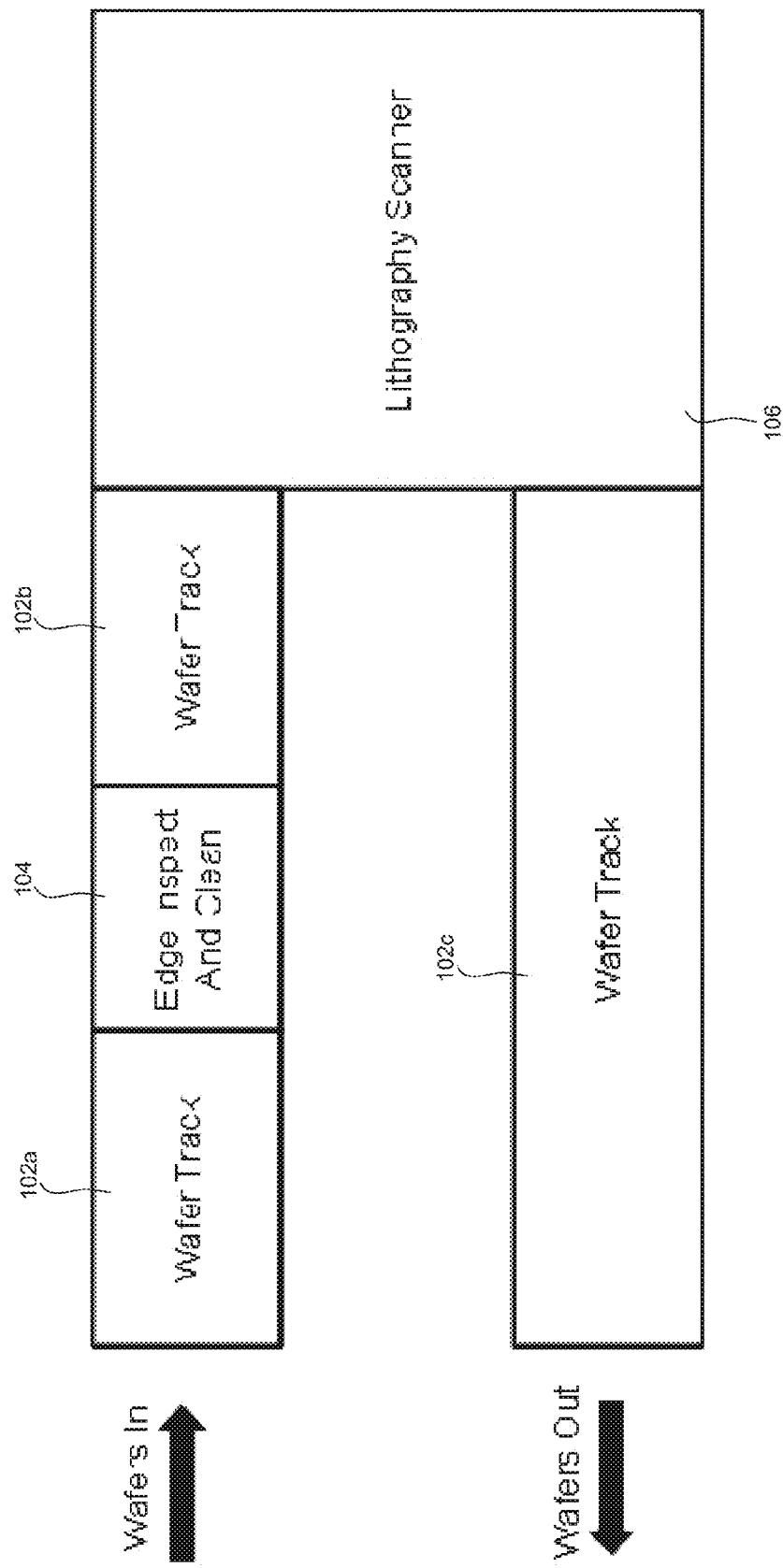
FIG. 1A is a diagrammatic representation of an edge detection system in-line with a lithographic system in accordance with one embodiment of the present invention.

In the following description, numerous specific details are set forth in order to provide a thorough understanding of the present invention. The present invention may be practiced without some or all of these specific details. In other instances, well known component or process operations have not been described in detail to not unnecessarily obscure the present invention. While the invention will be described in conjunction with the specific embodiments, it will be understood that it is not intended to limit the invention to the embodiments.

As used herein, the terms "specimen" and "sample" generally refer to a wafer or any other specimen having an edge on which defects of interest may be located. Although the terms "specimen", "sample", and "wafer" are used interchangeably herein, it is to be understood that embodiments described with respect to a wafer may be configured and/or used for inspection and imaging.

As used herein, the term "wafer" generally refers to substrates formed of a semiconductor or non-semiconductor material. Examples of a semiconductor material include, but are not limited to, monocrystalline silicon, gallium arsenide, and indium phosphide. Such substrates may be commonly found and/or processed in semiconductor fabrication facilities. Substrates also refer to glass, sapphire, or other insulator materials that are sometimes used in modern-day fabrication.

One or more layers may be formed upon a wafer. For example, such layers may include, but are not limited to, a resist, a dielectric material, and a conductive material. Many different types of layers are known in the art, and the term wafer as used herein is intended to encompass a wafer on which all types of layers may be formed. One or more layers formed on a wafer may be patterned. For example, a wafer may include a plurality of dies, each having repeatable pattern features. Formation and processing of such layers of material may ultimately result in completed semiconductor devices. In sum, a wafer may include a substrate on which a portion of the layers of a complete semiconductor device have been formed or a substrate on which all layers of a complete semiconductor device have been formed.

Wafers may contain defects in the edges. Examples of defects that may be found in the edge of wafers include, but are not limited to, chips, cracks, scratches, marks, particles, and residual chemicals (e.g., resist and slurry). For example, while spin-coating the wafer with photoresist material, a photoresist bead may form around the wafer perimeter and excess photoresist may migrate down over the edge of the wafer. Such excess edge photoresist may flake off and migrate to the device areas of the wafer or to the chuck or other surfaces of the lithography tool. Similarly, etch chemicals or deposition film materials may remain on the wafer edge and migrate to the device areas. Any number of these edge defects may result in yield loss. When multiple wafers are bonded together, the bond between such wafers may also have a defect.

The wafer's edge may be beveled or rounded along the entire length. Alternatively, the sample edge may include both a beveled edge portion and non-beveled edge portion, for example, in a bonded wafer type arrangement in which multiple wafers are stacked and bonded together. In both examples, the wafer edge may be subject to a grinding, cutting or polishing process that results in a beveled edge. During such grinding, cutting or polishing, a portion of the edge may remain unbeveled.

Wafer lithographic systems are subject to costly downtime for cleaning of particulates that are deposited on the chuck and immersion head. The lithography systems are high precision optical systems whose function requires extreme levels of cleanliness. As semiconductor fabrication techniques have become more complex, including the use of liquid immersion lithography, the risk of contaminants being displaced from the wafer edges to the lithography tool's critical surfaces has also risen. This contamination can cause significant loss of production as the fabrication line must be shut down for cleaning.

A source of many of these particulates is the edge region of wafers, including the top side within millimeters of the apex, the side bevels and apex region, and the bottom side within millimeters of the wafer apex. In terms used by the SEMI organization of San Jose, Calif., these zones are identified as Zone 1 through Zone 5.

This downtime cost could be significantly reduced if a wafer edge inspector could both operate at the same or higher throughput as the lithographic system. The wafer edge inspector could also provide the functionality of an in-line wafer pre-aligner, in which case the edge inspection system could take the place of the existing pre-aligner in the wafer track in-line before the lithography system in the fabrication flow. Some edge inspection systems, such as the KLA-Tencor Visedge system, currently obtain image data during the inspection process, and these systems can be configured to perform pre-alignment for lithography systems.

In certain embodiments, an edge inspection system is placed within the flow of a photolithography process. Preferably, the edge inspection system has a low cost and a small form factor that can be easily integrated into equipment that is part of the lithography system and flow. Additionally, the edge inspection is performed at a rate that does not affect or minimally affects the rate of the photolithography system.

Figure 1B:
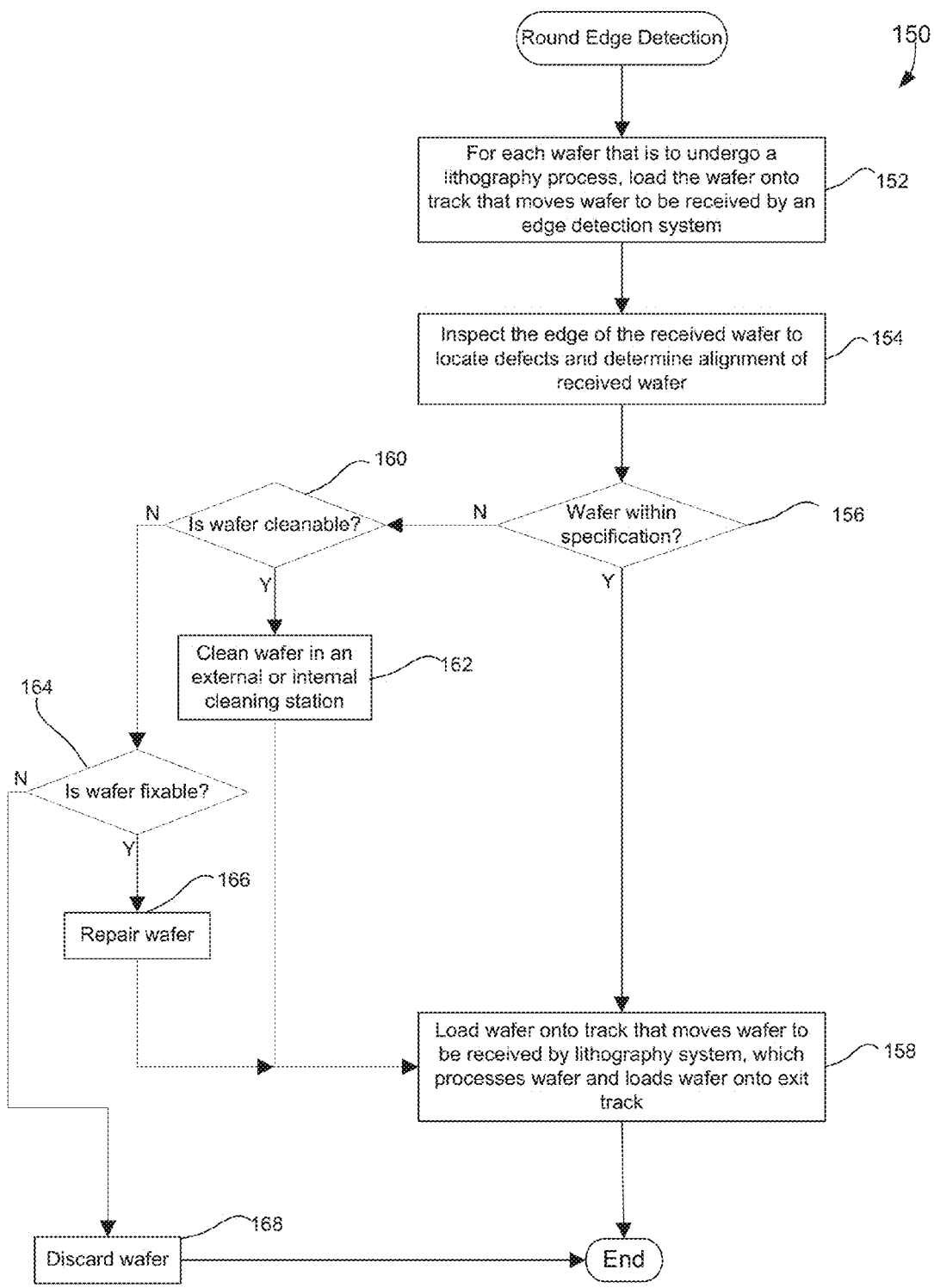
FIG. 1B is a flow chart illustrating an edge detection process in accordance with one embodiment of the present invention.

FIG. 1A is a diagrammatic representation of an edge detection system 104 that is in-line with a lithographic system 106 in accordance with one embodiment of the present invention. FIG. 1B is a flow chart illustrating an in-line edge detection process in accordance with one embodiment of the present invention. For each wafer that is to undergo a lithography process, the wafer is loaded onto a track (e.g., 102a) that moves the wafer to be received by a fast edge detection system 104 in operation 152. The edge of the received wafer is inspected to locate defects and determine an alignment of such wafer in operation 154. The edge inspection system 104 is configured to perform a fast edge inspection. For example, the edge of each wafer is inspected immediately prior to performing a subsequent photolithography process on such wafer.

Besides providing fast edge inspection, the edge inspection system 104 may replace a pre-alignment system for the lithography system so as to perform pre-alignment for such lithography system. The pre-alignment serves to identify the rotational orientation of the wafer on the track.

It may then be determined whether the wafer is within specification based on the edge inspection results in operation 156. For instance, the detected defects may be classified as "real" defects that can affect yield or cause contamination problems or may be classified as "false" defects that are unlikely to affect yield or cause contamination. In one defect detection implementation, defects are found by comparing local variations with surrounding areas and defining a difference that is above a predefined threshold as a "real" defect, determining whether the detected light is received by a particular type of channel (e.g., scattered vs. reflected), etc. As part of this process, it may also be determined whether the found edge defects are in a form that will likely contaminate the lithography system, which may cause the lithography system to be taken off-line for repair and/or cleaning and entail significant costs and delays.

If it is determined that the wafer is within specification, the wafer may then be loaded onto a track (e.g., 102b) that then moves the wafer to be received by the lithography system 106 in operation 158. Any potential defects may also be tracked as the wafer is processed so as to determine that the potential defects do not develop into "real" defects that will likely affect yield. For instance, the location of each potential defect is stored and such location is periodically inspected by an edge detection tool after the wafer is processed by one or more additional fabrication steps. After wafers are processed by lithography system 106, the wafers are then loaded onto an exit track 102c in operation 158. For instance, the wafer is output from this system via wafer track 102c.

If a wafer is determined to be potentially out of specification, it may then be determined whether the wafer is cleanable in operation 160. For instance, it may be determined whether the defects can be cleaned away from the edge of the wafer. If the wafer is cleanable, the wafer is then cleaned in an external cleaning station or internal cleaning station (104) in operation 162. After cleaning the wafer can then be loaded onto the track that moves the wafer to be received by the lithography system 106 in operation 158, and the lithography system 106 processes and outputs such wafer via track 102c in operation 158.

This type of an in-line edge inspection arrangement would allow wafers identified as potential particulate sources to be routed to either a built-in cleaning operation or an external cleaning station (not shown) before entering the scanner 106 via wafer track 102b, thus significantly reducing the need for scanner cleaning and downtime by extending the time between cleaning events. By replacing the existing pre-aligner system in the wafer track, this solution would minimize the impact to the wafer scanner apparatus. After wafers are processed by lithography system 106, the wafers are then loaded onto an exit track 102c in operation 158 so that the wafer is output from the lithography system 106 flow.

If the wafer is not cleanable, it may also be determined whether the wafer is fixable in operation 164. A wafer repair operation 166 may then be performed for fixable wafers. The repaired wafer can then be loaded onto the track to be received and processed by the lithography system in operation 158. If the wafer is not fixable, the wafer may instead be discarded.

Turning now to more detailed drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Certain embodiments of an edge detection system provide inspection for the edge regions of wafers, including the top edge, bevels and side, and bottom edge for particulates, in-line with semiconductor fabrication production lines at high throughput. For instance, the edge inspection is performed at a speed that is equal to or greater than the speed at which the lithography system processes wafers. In a specific implementation, wafers are processed by the lithography system at a rate of 200 wafers per hour. In this implementation, the edge inspector inspects wafers at a rate of 200 wafers per hour or more. The resulting inspection data may be used to route wafers to a cleaning step as needed, as well as providing wafer pre-alignment data to the lithographic system.

Figure 2A:
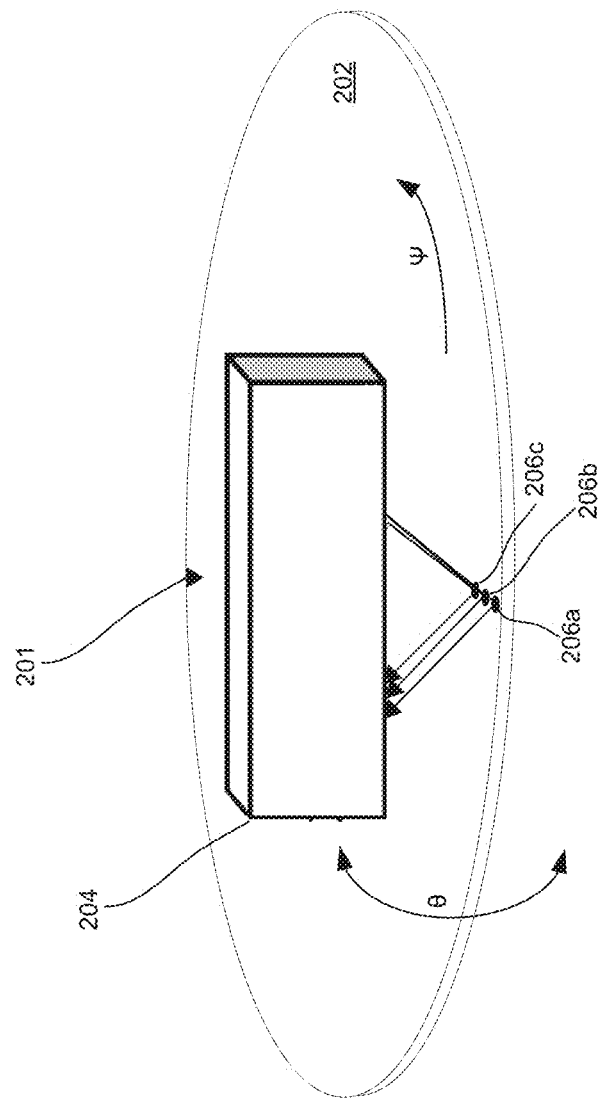
FIG. 2A~2C show one implementation of an edge detection system 204 having a multi-spot mode in accordance with one example implementation of the present invention.
Figure 2B:
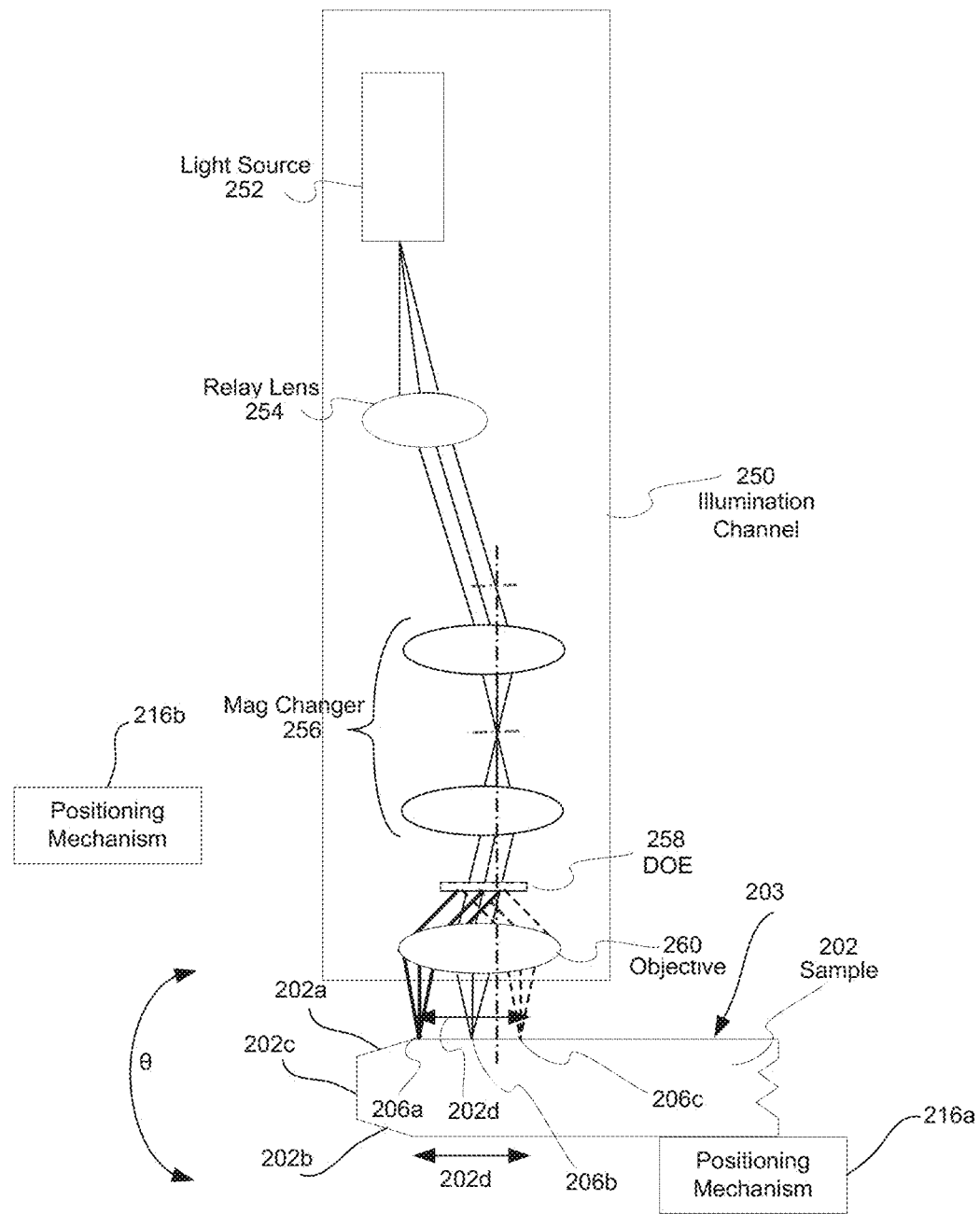
Figure 2C:
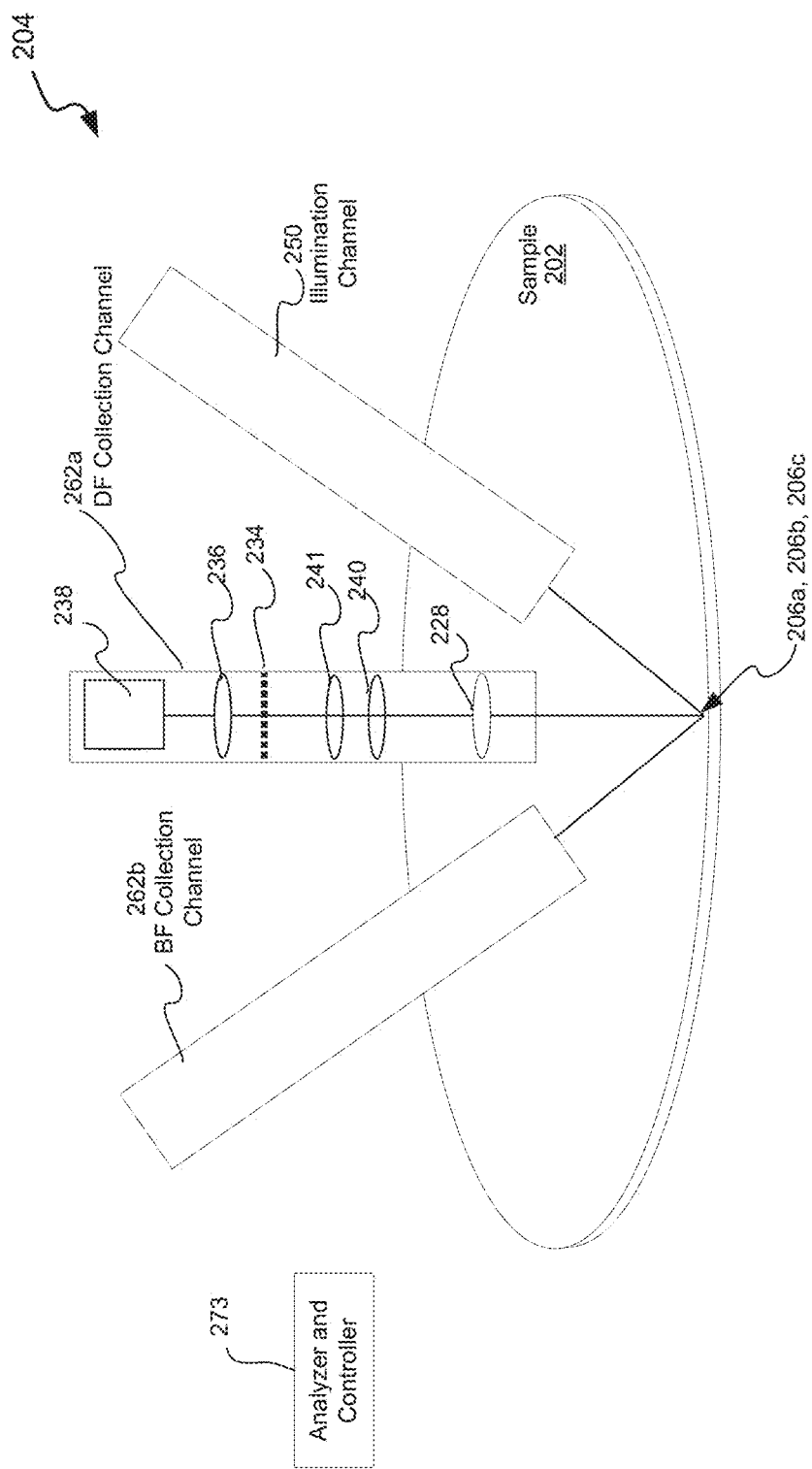

FIG. 2A~2C show one implementation of an edge detection system 204 having a multi-spot mode to inspect the wafer and measure the pre-alignment rotation of the wafer. FIG. 2A~2C are simplified diagrams and do not show every component that may typically be present in such a system so as to simplify the description. As shown in the perspective view of FIG. 2A, this edge detection system 204 generates multiple illumination beams that are focused at multiple spots 206a, 206b, and 206c on the sample 202. The edge detection system can detect defects on a rounded edge of sample, such as a beveled edge of a semiconductor wafer. In this example, a cross-sectional beveled edge portion of a wafer 202, which is the thinnest edge surface of a semiconductor wafer, is illustrated as the sample of interest. The sample's top surface 203 (FIG. 2B) may include one or more patterned layers or may be bare. The wafer may further include at least a portion of an integrated circuit, a thin-film head die, a micro-electro-mechanical system (MEMS) device, flat panel displays, magnetic heads, magnetic and optical storage media, other components that may include photonics and optoelectronic devices such as lasers, waveguides and other passive components processed on wafers, print heads, and bio-chip devices processed on wafers. In this example, the beveled edge has top surface 202a, bottom surface 202b, and side surface 202c. The top and bottom surfaces 202a and 202b slope into the side surface 202c. However, the rounded edge may be formed by any suitable number of beveled facets.

This edge detection system 204 may be moved along actuator path $\theta$ to scan the edge of the sample 202 of FIG. 2B. This movement may be accomplished by one or more positioning mechanisms (e.g., 216b) that are mechanically coupled to one or more components of the edge detection system 204. In some embodiments, the edge detection system 204 may be supported by a stage coupled to the one or more actuators or positioning mechanisms 216b. The one or more positioning mechanisms 216a are configured to radially and rotationally actuate the edge detection system 204 along the actuation path (over and under a portion of the sample 202) to enable scanning across the selected portion of the sample edge 202a~202e.

Additionally, the sample may be rotated in direction $\Psi$ to inspect different edge portions of sample's circumference. The sample may be supported by a stage configured to actuate the sample 202 to a selected position (e.g., placing a defect of interest into view). For example, the stage may be mechanically coupled to or include one or more motors, servos, or alternative positioning mechanism 216a configured to spin the sample 202 about its central axis to place a selected portion of the sample edge (e.g., 202a~202e) into view.

The positioning mechanisms described herein may take any form, such as a screw drive and stepper motor, air-bearing drive, linear drive with feedback position, or band actuator and stepper motor. In general, the edge detection system simultaneously inspects multiple positions of the sample edge corresponding to the spots. The sample can then be rotated with respect to this edge detection system so that the entire circumference at the current positions of the multiple spots is inspected as the sample rotates. The edge detection system can then be rotated or stepped in direction $\theta$ so as to inspect positions between the last spots and along the entire sample circumference as the sample rotates. This stepping process is repeated until all the edge portions along direction $\theta$ are covered.

FIG. 2B is a diagrammatic side view of an illumination channel 250 for the edge detection system 204 of FIG. 2A in accordance with one embodiment of the present invention. As shown in FIG. 2B, the illumination channel 250 may include one or more light sources (e.g., 252) for generating one or more illumination beams. The wavelength of the illumination beam depends on the particular requirements of the application.

A relay lens 254 receives the generated illumination and produces a real pupil at a pupil plane. A magnification changer 256 can be used to adjust the size of the spot and the length of sweep.

In the illustrated embodiment of FIG. 2B, a diffractive optical element (DOE) 258 can be positioned before magnifier changer 256 to generate a plurality of spots. Although FIG. 2B shows three spots being generated, other embodiments can generate a different number of spots. The illustrated 3×1 DOE elements for generating multiple beams may be replaced by any suitable DOE or, more generally, any n×m DOE. An objective lens 260 can then be used to focus the spot onto a sample 202, such as a wafer edge.

Alternatively, the system may utilize a relay lens located between the DOE 258 and objective lens 260. When the pupil of the illumination system is physically located at the objective and inside the lens assembly, a relay is typically used to form a real pupil outside the objective so that the DOE may be placed at such pupil. For low numerical aperture systems, the physical stop location will be outside the objective lens assembly. For high numerical aperture systems the physical stop may be located within the objective lens assembly. In this case, an additional relay would be added to the system to provide a location at which to place the DOE.

The illumination path may include other optical elements, such as a relay lens for collimating the incident beam, analyzer for polarization, waveplates for providing any linear or circular polarizations (e.g., S, P, etc.), and any number of mirrors and beam splitters for forming both normal and oblique incident beams. Any of the mirrors or beam splitters may be movable (e.g., actuated).

The optical axis of each oblique incident beam may be directed onto the sample surface at an angle, such as in the range of 0-85 degrees with respect to the normal to the sample surface, depending on the particular application. Multiple oblique angles may be achieved by translation of one or more mirror or beam splitter components. Incident oblique light may come in at an oblique angle from a tilted objective with respect to the sample surface.

FIG. 2C illustrates a perspective view of the illumination channel 250, a dark field (DF) collection channel 262a, and a bright field (BF) collection channel 262b of a multi-spot edge detection system 204 in accordance with one embodiment of the present invention. The DF and BF collection channels may include any suitable optical elements for directing scattered and specular light from the sample towards one or more sensor/detectors. The BF channel 262b may include similar components as the DF channel. In general, the system 204 may include separate BF and DF collection channels or a merged BF and DF channel so as to share one or more components in accordance with an alternative of the present invention.

The DF channel 262a can be used to collect scattered light from the sample 202 in response to illumination being directed towards such sample 202. Light directed at the DF channel 262a may be transmitted through lens 228, lenses 240 and 241, Fourier filter and configurable aperture assembly 234, and lens 236 and be directed towards sensor module 238. The collection path may also include a polarization analyzer assembly.

Light that is scattered from the surface is collected and collimated through lens assembly 228. Lens assembly 228 may include multiple optical elements so as to produce a real accessible collection pupil. This collimated light may then be transmitted through lens 240 and 241, which may be configured to relay the collected light towards a Fourier plane. Fourier filter and flexible aperture mechanism 234 may be configured to spatially filter portions of the output light at the Fourier plane. In addition, mechanism 234 may include a programmable aperture system for transmitting various spatial portions at the Fourier plane to maximize signal and/or minimize noise (and resulting angles with respect to the normal optical axis) of the output beam.

The output normal beams may then be focused by lens 236 onto sensor module 238. The sensor module 238 may include a spot or beam separation assembly, such as a slit and prism assembly for separating each output beam. For instance, each spot passes thru the slit and then into a prism, which is used to both separate the spots and homogenize the light. The output light for each beam may then be output from its corresponding prism onto a fiber optics element for passing the output beam towards focusing element, which focuses its output beam onto a sensor. Each fiber optics element provides further homogenization of the beam and enables the output to be directed onto a separate sensor for each spot. The function of the fiber could also be accomplished using mirrors, prisms or the like. Each fiber randomizes the received output light. Other isolation mechanisms may be used, besides utilizing a slit, prisms, and/or optical fibers. Each sensor can take the form of a PMT, avalanche photodiode, pin diode, CCD camera, etc. For example, a photodiode (or photodiode array) may be used in the BF channel, while a PMT is used in the DF channel.

Mechanisms for increasing dynamic range of the detected signals may be provided in proximity to collector channels. In general terms, a high dynamic range collector includes a light sensor, such as a photomultiplier tube (PMT), for generating a signal from detected photons and an analog to digital converter (ADC) for converting the light signal to a digital light signal. Of course, other suitable mechanism may be used for sensing light and converting an analog signal into a digital signal. A gain adjustment feedback system may also be used to adjust the gain of each PMT.

The DF collection channel 262a may collect light over a fixed solid angle over a region which is approximately perpendicular to the plane of the sample surface, or may collect light from a non-perpendicular angle. The DF collection channel 262a may be used to collect scattered light from the intentional patterns on the wafer, as well as to detect defects which scatter light in an upwards direction. Signals collected from the sample's intentional patterns, such as alignment notch 201 of FIG. 2A, may be used to facilitate the alignment and registration of the wafer pattern to the coordinate system of the mechanical stage in the instrument. Any defects are found relative to an alignment mark 201. Once the alignment mark 201 is found and known, this alignment mark's position can also be used to align the wafer relative to the reticle pattern when the wafer is loaded into the lithography system. For instance, the alignment mark's position with respect the wafer is found in the edge detection system and then tracked as the wafer moves from the edge detection system and enters the lithography system. This general alignment process can be performed by any of the other edge detection systems described further below.

Mechanisms for maintaining each spot to be focused at a same relative position on the surface edge can also be implemented into any of the edge detection embodiments described herein. Several example embodiments of mechanisms for maintaining a fixed distance between an edge inspection head and the edge surface as the beam is moved over the edge surface are disclosed further in U.S. Pat. No. 7,656,519, issued 2 Feb. 2010 by Meeks et al., which patent is incorporated herein by reference in its entirety. This incorporated patent also describes methods for detecting defects, which can be implemented with any of the system embodiments described herein.

Figure 3A:
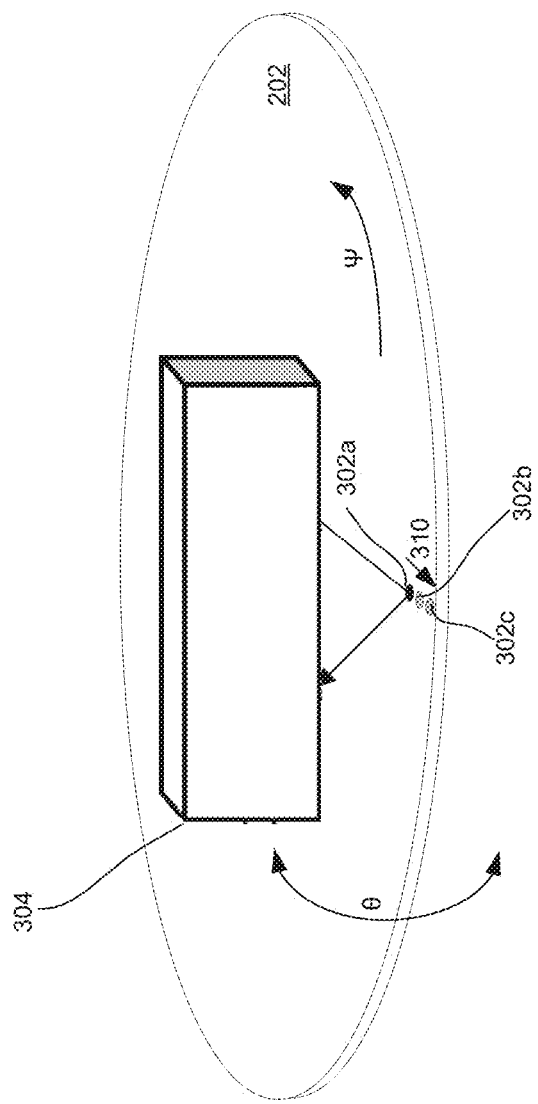
FIGS. 3A~3D illustrate an edge detection system with an acousto-optical device (AOD) scanner in the illumination beam path in accordance with another implementation of the present invention.

FIGS. 3A~3D illustrate an edge detection system with an acousto-optical device (AOD) scanner in the illumination beam path in accordance with another implementation of the present invention. Adding an AOD allows the relatively flat regions on the top and bottom of the wafer near the edge to be scanned in a single rotation of the wafer, as opposed to the current track-at-a-time method which requires on the order of 1000 rotations of the wafer in these regions. As shown in FIG. 3A, the edge inspection system 304 generates a single spot 302a that scans across the surface in direction 310, for example, to spot positions 302b and 302c. The sample 202 may also then rotate in direction Ψ to a next edge portion along the circumference.

Figure 3B:
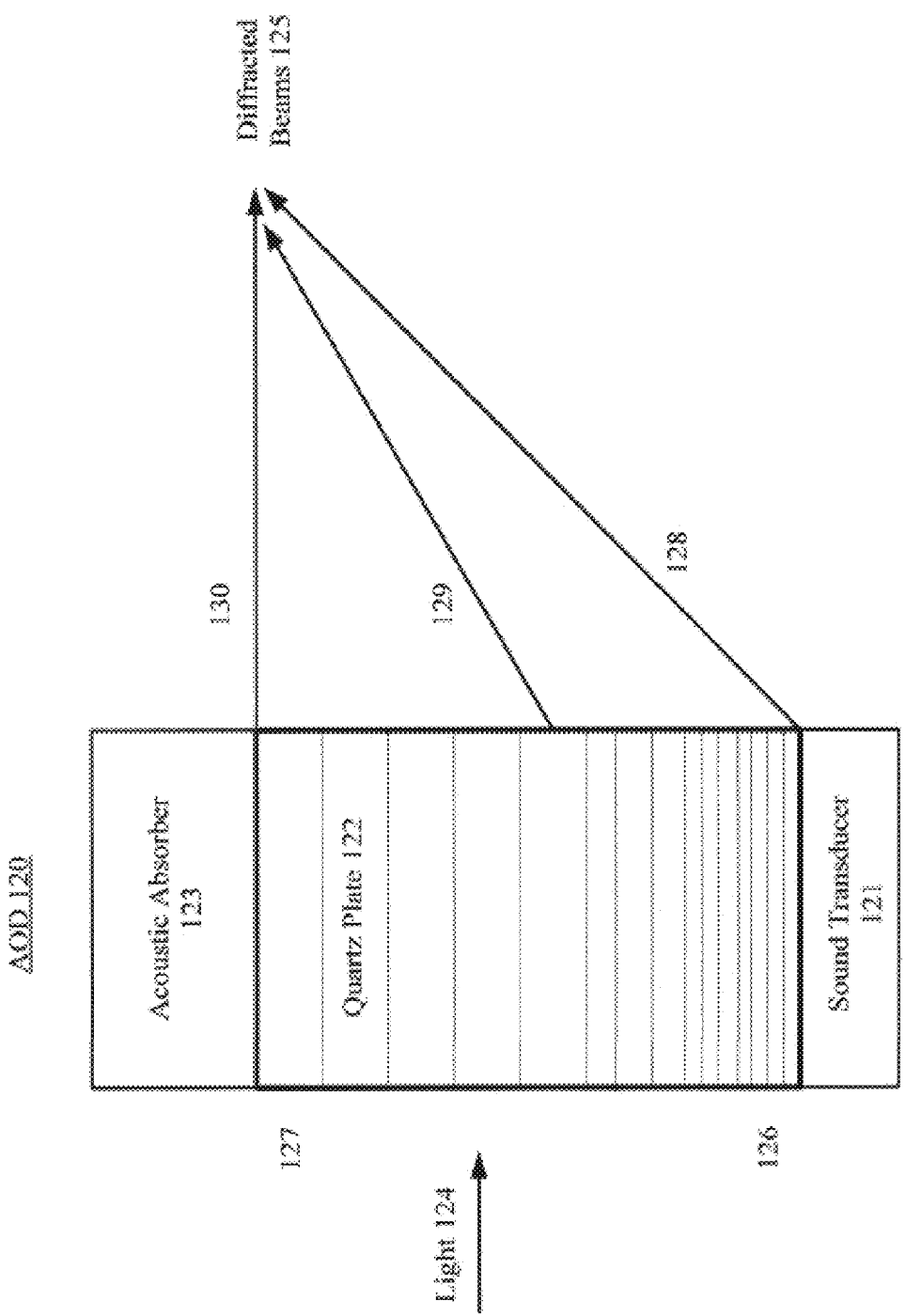

Some scanning and deflection systems include an illumination channel having one or more incident beam sources for scanning or sweeping one or more beams across the wafer. The scanning system may specifically include an acousto-optic deflector (AOD) and a mechanism for controlling the AOD's deflection characteristics. For instance, a clock may be used to generate a "chirp" signal input to each AOD. For example, FIG. 3B illustrates a simplified configuration of an acousto-optical device (AOD) 102. AOD 102 includes a sound transducer 121, an acousto optic medium such as quartz 122, and an acoustic absorber 123. Other acousto optic medium materials, besides quartz, can be utilized, depending on the particular wavelength requirements of the system. The acoustic absorber could be a cut in the acousto optic medium 122. An oscillating electric signal can drive sound transducer 121 and cause it to vibrate. In turn, this vibration creates sound waves in quartz plate 122. Acoustic absorber 123 can be formed from a material that absorbs any sound waves that reach the edge of quartz plate 122. As a result of the sound waves, incoming light 124 to quartz plate 122 is diffracted into a plurality of directions 128, 129 and 130.

A diffracted beam emerges from quartz plate 122 at an angle that depends on the wavelength of the light relative to the wavelength of the sound. By ramping frequencies from low to high, portion 126 may have a higher frequency than portion 127. Because portion 126 has a higher frequency, it diffracts a portion of the incident light beam through a steeper angle as shown by diffracted beam 128. Because portion 127 has a relatively lower frequency, it diffracts a portion of the incident light beam through a more shallow angle as shown by diffracted light beam 130. Because a mid-section portion between portions 126 and 127 has a frequency between the higher and relatively lower frequencies, it diffracts a portion of the incident light beam through an intermediate angle as shown by diffracted light beam 129. Thus, an AOD can be used to focus an incoming beam 124 at position 125.

Figure 3C:
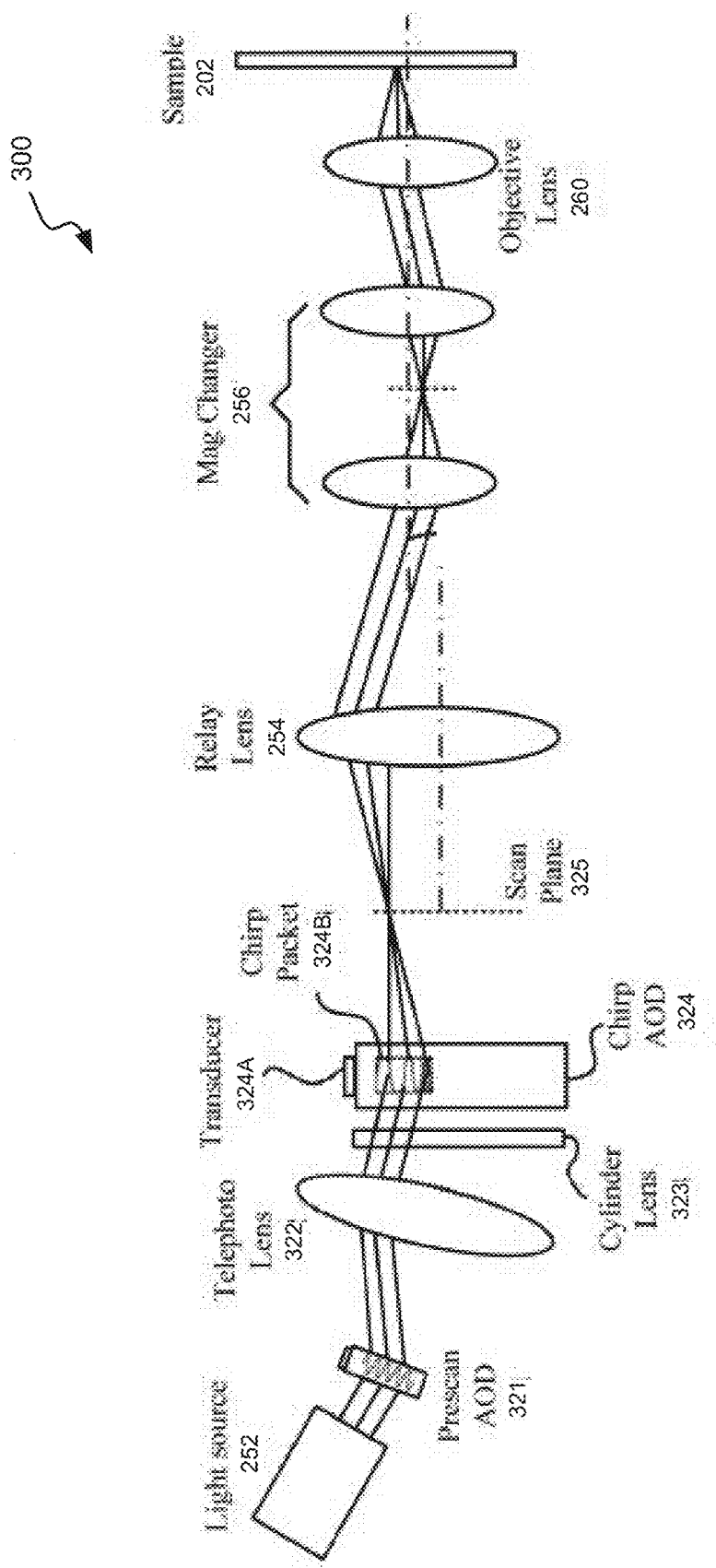

FIG. 3C illustrates an exemplary dual AOD illumination system 300 configured to generate and scan a beam across a sample 202, such as a wafer. A prescan AOD 321 can be used to deflect the incident light from a light source 252 at an angle, wherein the angle is proportional to the frequency of the radio frequency (RF) drive source. A telephoto lens 322 can be used to convert the angular scan from prescan AOD 321 into a linear scan.

Figure 3D:
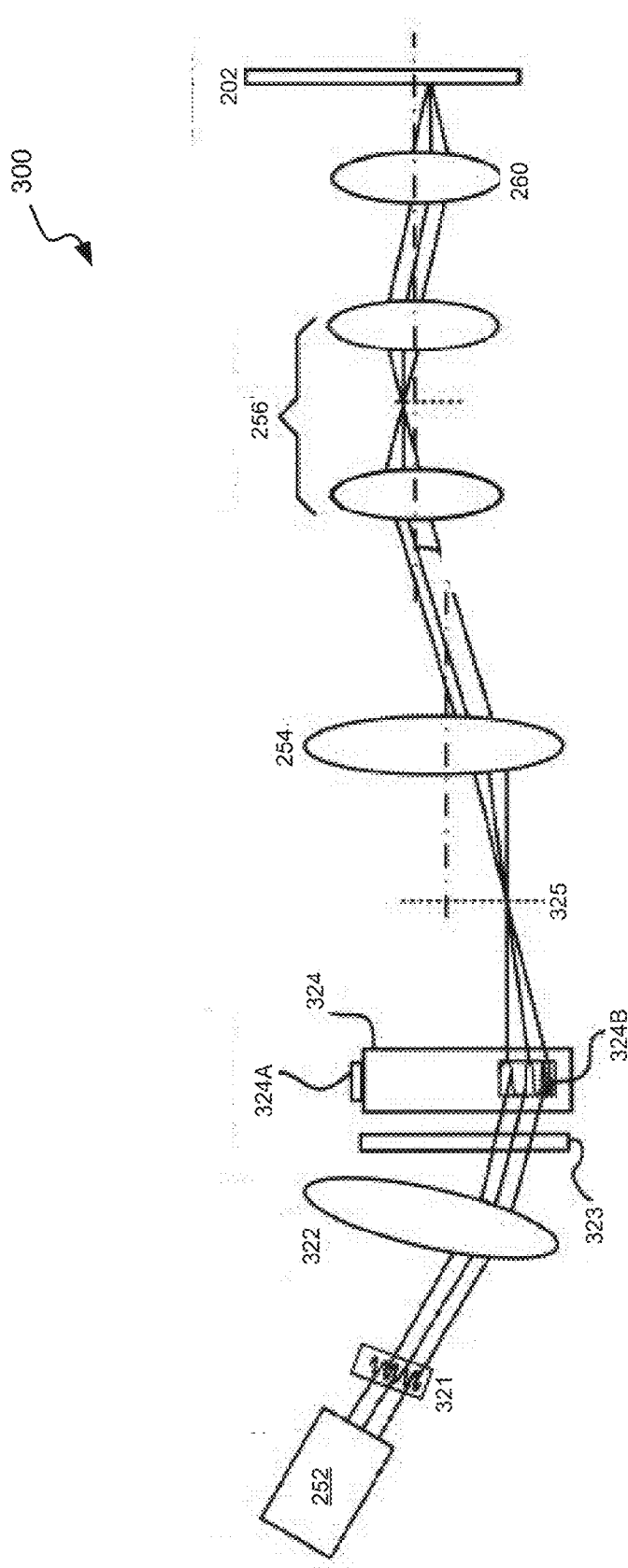

A chirp AOD 324 can be used to focus the incident beam in the plane of acoustic propagation onto a scan plane 325, which can be accomplished by ramping thru all the RF frequencies with transducer 324A. This rapid ramping forms a chirp packet 324B. Chirp packet 324B then propagates thru chirp AOD 324 at the speed of sound. FIG. 3C shows the location of chirp packet 324B at the start of a spot sweep, whereas FIG. 3D illustrates the location of chip packet 324B at the end of that spot sweep. Note that during this propagation, prescan AOD 321 can adjust its RF frequency to track the chirp packet in AOD 324 to keep the light beam incident upon chirp packet 324B.

A cylinder lens 323 can be used to focus the beam in a plane perpendicular to the plane of acoustic propagation. A relay lens 254 can be used to generate a real pupil at a pupil plane. A magnification changer 256 can be used to adjust the size of the spot and the length of sweep. An objective lens 260 can then be used to focus the spot onto a sample 202, such as a wafer.

Other systems may utilize a beam expander in place of the pre-scan AOD to form a "flood AOD" system. In a flood AOD configuration (not shown), a single or multiple chirp packets (not shown) can be generated in AOD 324. Since the entire AOD is flooded with light from the beam expander, AOD 324 focuses the light incident on each chirp packet and, thus, each chirp packet generates its own spot. Therefore objective lens 260 focuses one or more spots onto sample 202 simultaneously (not shown).

Figure 4A:
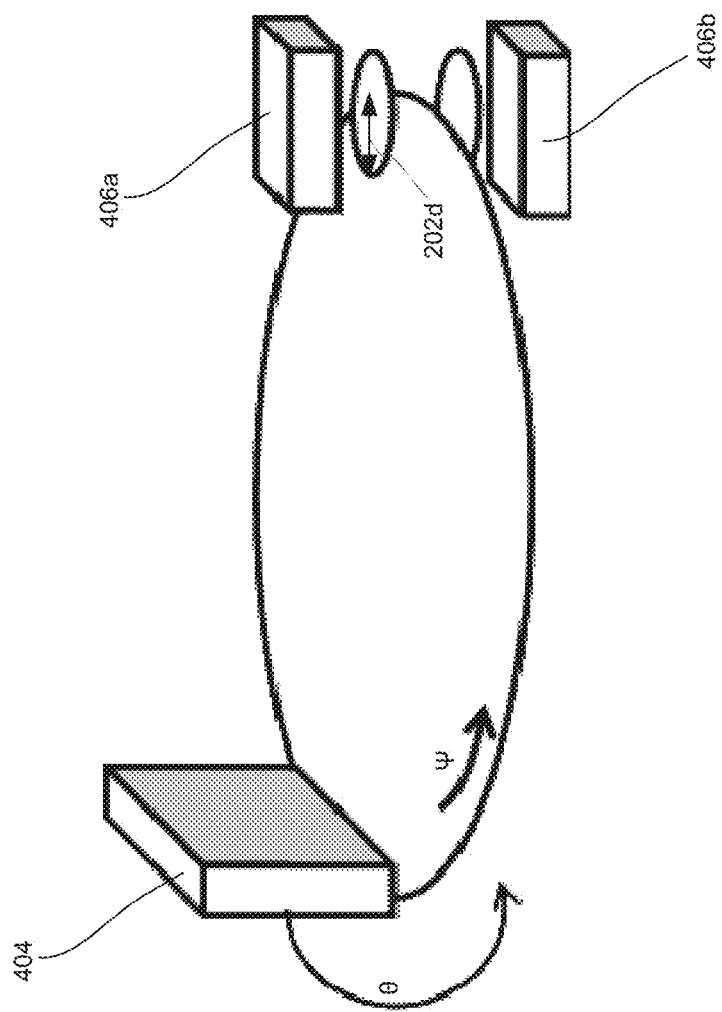
FIGS. 4A~4C are diagrammatic representations of an edge inspection system having a spot scanner for the edge surfaces and two cameras for the top and bottom surfaces, respectively, in accordance with another embodiment of the present invention.

When an AOD that produces multiple chirp packets is used to generate multiple spots, a larger AOD is needed since each chirp packet has a finite size as a result of the time required to ramp through the required RF frequencies. The more chirp packets; the larger the AOD that is used. Additionally, each of the chirp packets is attenuated as it travels along the length of the AOD. Thus, a larger AOD results in larger attenuation losses than a smaller AOD. Conversely, an AOD that has closer multiple chirp packets and, thus, scanning spots in close proximity to one another results in more crosstalk between scanning spots FIG. 4A is a diagrammatic representation of an edge inspection system 400 having an edge inspector 404 for the edge surfaces and two cameras 406a and 406b for inspecting the top and bottom surfaces (e.g., 202d and 202e), respectively, in accordance with another embodiment of the present invention. The edge inspector 404 could be in the form of a single spot or multi-spot scanner as described above. The edge inspector 404 may move along an actuator rotational path that follows the edge of the sample 202 along direction θ, excluding the top and bottom surfaces. The edge inspector 404 may also incorporate a deflector mechanism, such as an AOD, that scans one or more spots across the edge. These top-side and bottom-side spot scans could be replaced with line-scan camera or TDI (time delay integration) camera inspections (e.g., 406a and 406b), so that a single-rotation of the wafer (e.g., in direction Ψ) could be employed to inspect those regions and provide more sensitivity.

Figure 4B:
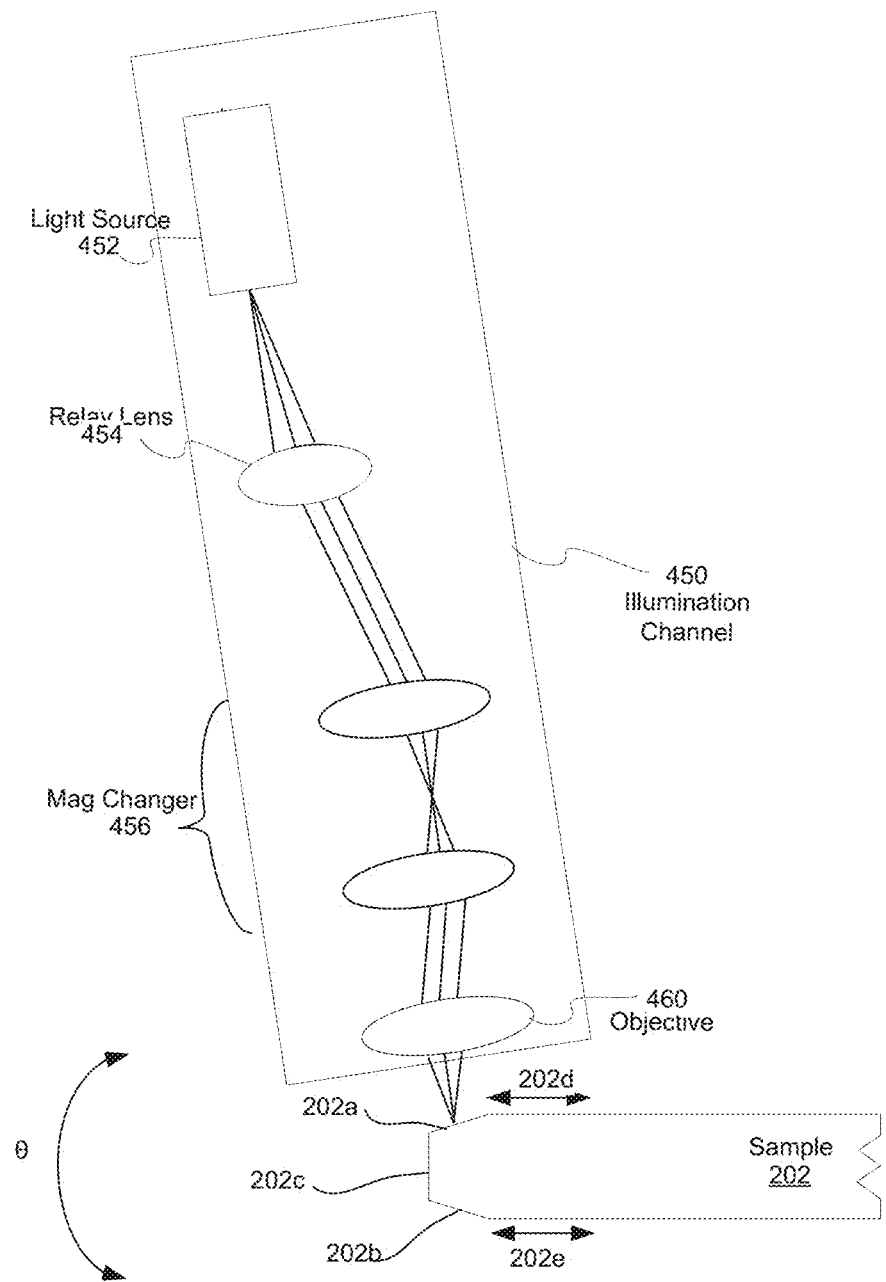

FIG. 4B is a diagrammatic side view of an illumination channel 450 of the edge inspector 404 for inspecting the edge surfaces in accordance with a specific implementation of the present invention. As shown, the illumination channel 450 may include a light source 452 for generating an illumination beam, a relay lens 454 for producing a real pupil at a pupil plane, a magnifier changer 456 for selecting different magnification settings, and objective 460 for focusing the illumination beam onto each edge of the sample 202, such as beveled edges 202a~202c, as the illumination channel is rotated over such edge. The top and bottom cameras 406a and 406b are positioned at a different circumference location from the edge inspector channel 460 so as to simultaneously image portions of the top and bottom border regions 202d and 202e as the sample rotates in direction Ψ (FIG. 4A).

Figure 4C:
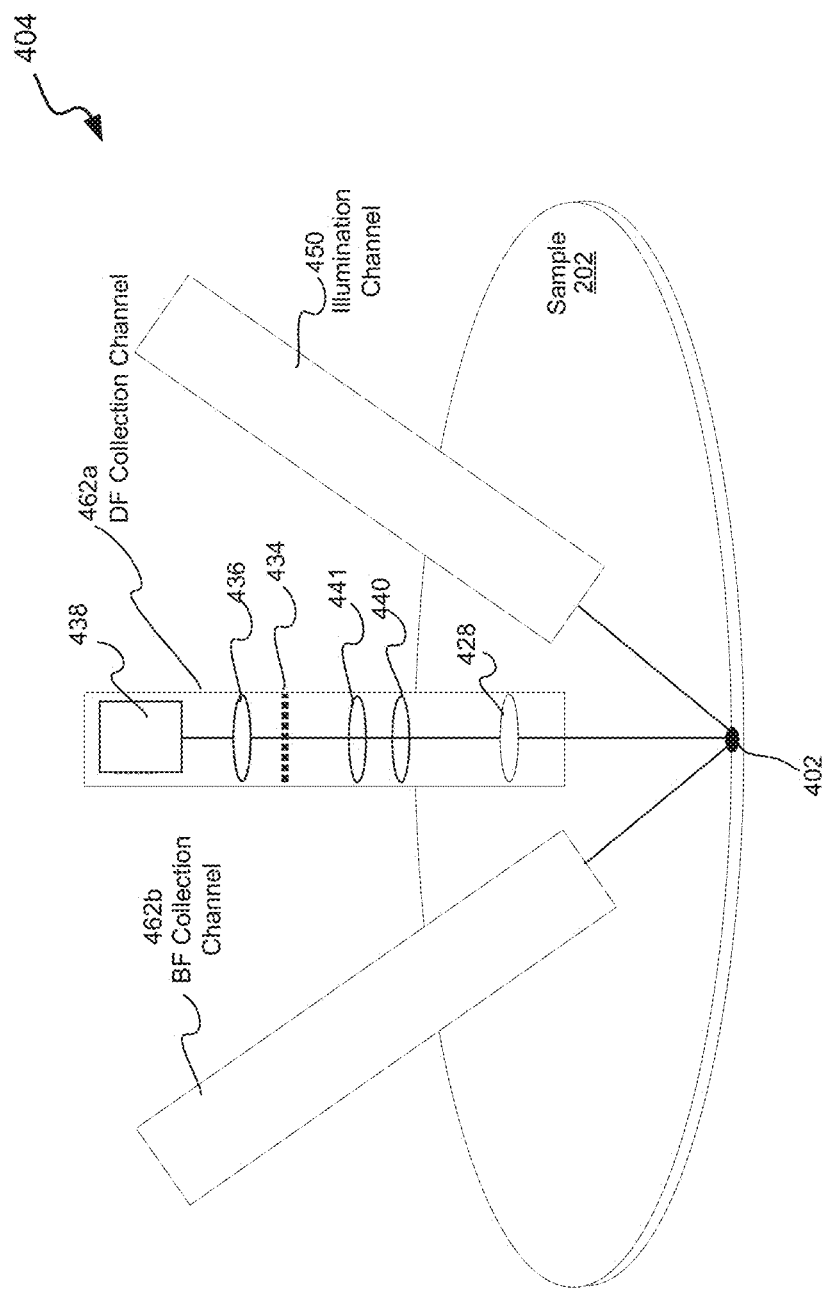

FIG. 4C illustrates a perspective view of the illumination channel 450, a dark field (DF) collection channel 462a, and a bright field (BF) collection channel 462b of the edge detection system of FIG. 4A. The DF and BF collection channels may include any suitable optical elements for directing scattered and specular light from the sample towards one or more sensor/detectors. The BF channel 462b may include similar components as the DF channel. In general, the system 404 may include separate BF and DF collection channels or a merged BF and DF channel so as to share one or more components in accordance with an alternative of the present invention.

The DF channel 462a can be used to collect scattered light from the sample 202 in response to illumination being directed towards such sample 202. Light directed at the DF channel 462a may be transmitted through lens 428, lenses 440 and 441, Fourier filter and configurable aperture assembly 434, and lens 436 and be directed towards sensor module 438. The collection path may also include a polarization analyzer assembly. These components may function similar to the same-named components as described above.

The top and bottom camera systems 406a and 406b may be configured in any suitable manner so as to image the top and bottom surfaces as the sample is rotated, for example, in direction Ψ.

Figure 5:
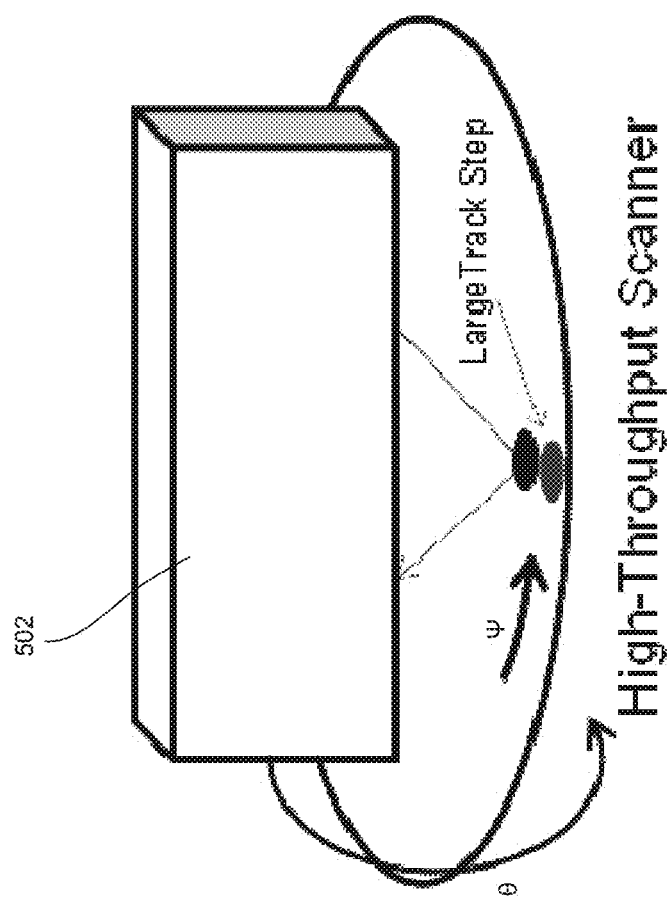
FIG. 5 is a diagrammatic side view of an edge inspection system for optimization of the scanning track size in accordance with another embodiment of the present invention.

FIG. 5 is a diagrammatic side view of an edge inspection system 502 for optimization of the scanning track size in accordance with another embodiment of the present invention. This system 502 may be configured to scan a single, large spot across the top surface, side surfaces, and bottom surface, for example, in direction θ. The sample 202 may also be rotated in direction Ψ. This system 500 can take larger steps along direction θ since the spot size covers more area on the sample. In this way, an optimum trade-off of sensitivity vs speed can be achieved. The system 502 may be configured in a similar manner as the single-spot systems described above. Additionally, this system 502 may be configured to generate a relatively large spot so as to achieve a higher throughput than other smaller spot-sized systems by any suitable mechanism, such as an adjustment of the focal length of the lens, adjusting how much the illumination beam is collimated, etc. The illumination spot may also be non-circular as, for example, an elliptical spot in order to result in an optimum sensitivity vs speed. This system 500 may alternatively be used to move more slowly to acquire more finely-resolved information at each spot.

Figure 6B:
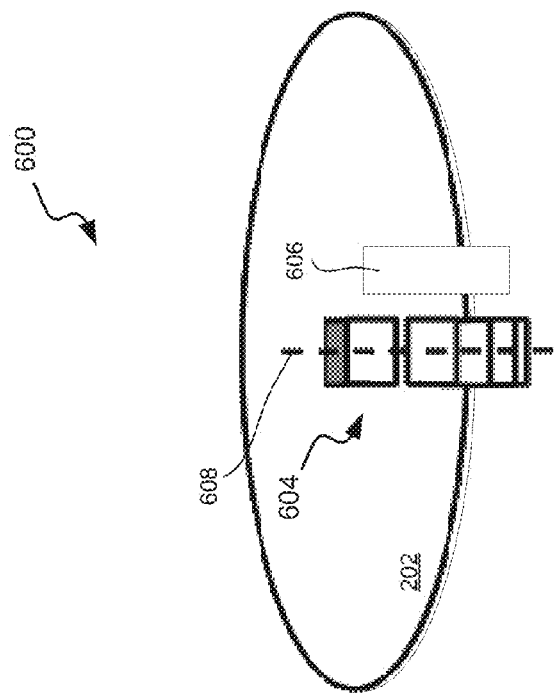
FIG. 6B is a side view of the system of FIG. 6A as seen from the back of the cameras and looking towards the edge-of-interest.
Figure 6A:
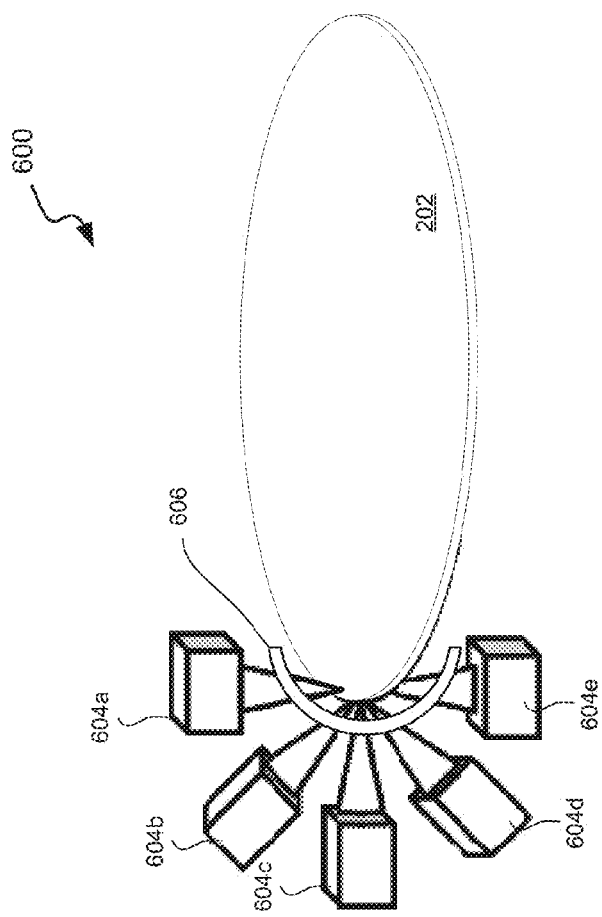
FIG. 6A is a diagrammatic side view of an edge detection system having multiple cameras in accordance with another specific implementation of the present invention.
Figure 6C:
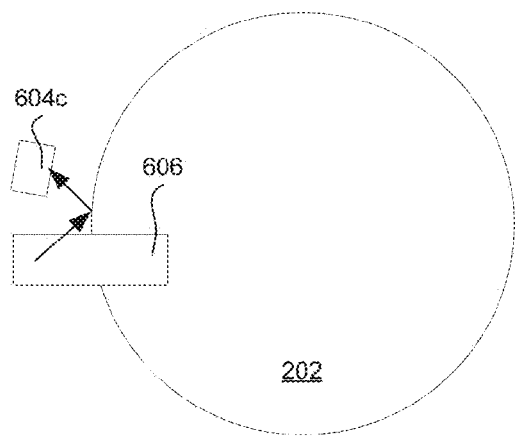
FIG. 6C illustrates a top view of the system of FIG. 6A.

FIG. 6A is a diagrammatic side view of an edge detection system 600 having multiple cameras in accordance with another specific implementation of the present invention. FIG. 6B is a side view of the system of FIG. 6A as seen from the back of the cameras and looking towards the edge-of-interest. FIG. 6C illustrates a top view of the system of FIG. 6A. As shown, the system 600 can include any suitable number of cameras 604 that are positioned along the top, side, and bottom edge, for example, along line 608, and these cameras are positioned to simultaneously receive light scattered and/or reflected from multiple positions on the top, side, and bottom surfaces in response to incident light that is directed towards such same surfaces by illuminator 606. In the illustrated example, camera 604a is positioned to receive light from the top surface, and camera 604e is positioned to receive light from the bottom surface. Cameras 604a, 604b, and 604c are positioned to receive light from the side surfaces, such as any number and type of beveled edges.

The illuminator 606 may take any suitable form to direct light towards the top, bottom, and side surfaces of the sample. As shown in FIGS. 6A-B, the illuminator 606 is in the form of an LED ring illuminator. In a specific implementation example, the multi-camera KLA-Tencor Wafer Edge Review (WER) system (available from KLA-Tencor of Milpitas, Calif.) can be reconfigured into a flash-on-the-fly image collection mode to inspect the wafer and measure the pre-alignment rotation of the wafer.

In the illustrated example, the illuminator 606 is in the form of an LED ring illuminator although any suitable type of illumination generators may be implemented with multiple cameras. For example, any of the illumination channels described herein may be utilized with a plurality of receiving cameras.

Figure 6D:
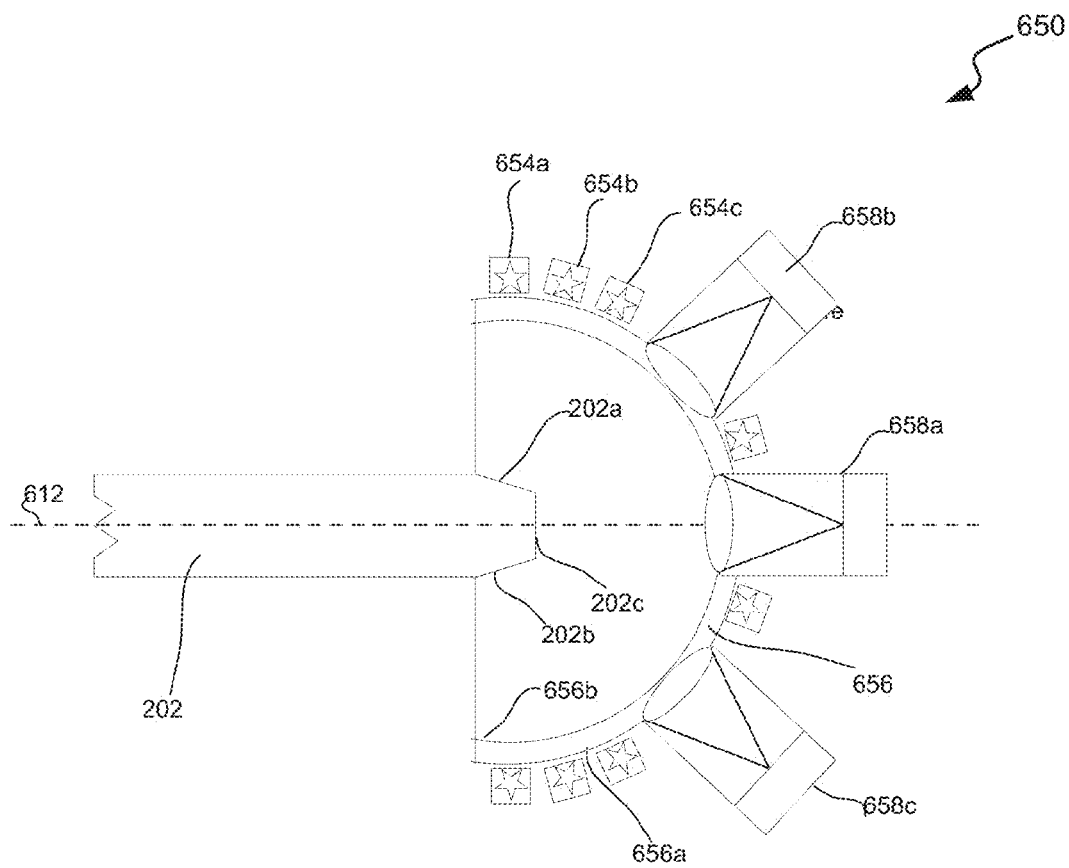
FIG. 6D is a cut-away side view of an edge detection system having multiple cameras and a curved diffuser in accordance with another embodiment of the present invention.

In another embodiment, LED light sources are coupled to the back of a curved diffuser as described in co-pending U.S. application Ser. No. 14/731,861, filed 5 Jun. 2015 by Paul D. Horn, which application is incorporated herein by reference in its entirety. FIG. 6D is a cut-away side view of an edge detection system 650 having multiple cameras and a curved diffuser in accordance with another embodiment of the present invention. As shown, multiple cameras (e.g., 658a, 658b, and 658c) may be positioned within the diffuser 656. Each camera or sensor 658 may also be positioned so as to receive scattered light from a particular set of one or more surfaces of the beveled edge (e.g., 202a~c).

In the illustrated example of FIG. 6D, the edge detection system 650 may be formed from a plurality of light sources (e.g., 654a, 654b, 654c) that are coupled with or adjacent to a back surface 656a of a dome-shaped diffuser 656. Any suitable light sources that are very compact may be used. Example light sources include LED's (light emitting diodes), one or more light sources coupled with fiber optics, such as halogen lamps, diode lasers, etc.

Each sensor or camera 658 generally includes collection optics for directing and focusing a portion of the light that was scattered from the edges-of-interest onto a detector/sensor. Each camera 658 may be integrated into the diffuser 656. For instance, the sensor 108 can be mounted or bonded within a hole or slot of the diffuser 656. The camera can mounted or bonded to be flush against the diffuser's internal surface 656b or be recessed below the diffuser surface. In certain embodiments, the image sensors are each very compact. For instance, each sensor may have a diameter that is less than or equal to a few mm. Example sensors include the OmniVision OV6922, etc.

The different cameras may be utilized for any number of applications. For instance, each camera may be placed at a different angle with respect to the surface of interest. Each camera may also be configured to detect a particular range of wavelengths or colors. Of course, cameras that each are configured to detect multiple colors may alternatively be used in this embodiment or any embodiment described herein.

The diffuser 656 may be formed from a material that transmits and scatters (e.g., diffuses) light from the light sources so that light is scattered from the entire inner portion of the diffuser towards the beveled edge surfaces in a wide range of angles. The diffuser 656 may be machined from an optically diffuse material, such as fluoropolymer or Spectralon available from Labsphere, Inc. of North Sutton, N.H., polycarbonite resins, etc. Alternatively, the diffuser 656 can be generated with a 3D printer. The diffuser may also be formed from a diffuser film adhered to a transparent substrate that is positioned between the light sources and film. The internal surface of the diffuser 656b may also be coated with a reflective material so as to reflect the diffused light towards the inside of the dome and towards the beveled edge surfaces.

The diffuser may have any suitable shape so as to provide a surface through which illumination beams from the light sources may be transmitted and scattered so that light is emitted towards all surfaces or a substantial portion of all surfaces of the beveled edge. In the illustrated example, the diffuser 656 is dome-shaped into a size to cover the range of angles of incidence of the light sources.

The light sources (e.g., 654) may be attached or positioned adjacent to the diffuser 656 in any suitable manner. Preferably, the distance between the light sources and the diffuser's external surface (e.g., 656a) has a range between 3 mm to about 1 inch. For example, LED's may be bonded to the external diffuser surface (e.g., 656a) that is opposite the internal diffuser surface (e.g., 656b), which faces the edge of interest.

In a specific implementation, the edge detection system 650 is positioned so as to provide illumination to all of the beveled edge surfaces and up to 10 or more mm into the border region on the top surface. It is also noted that the light is output from the entire surface of the dome to completely impinge on all sides of the beveled edge.

Figure 7B:
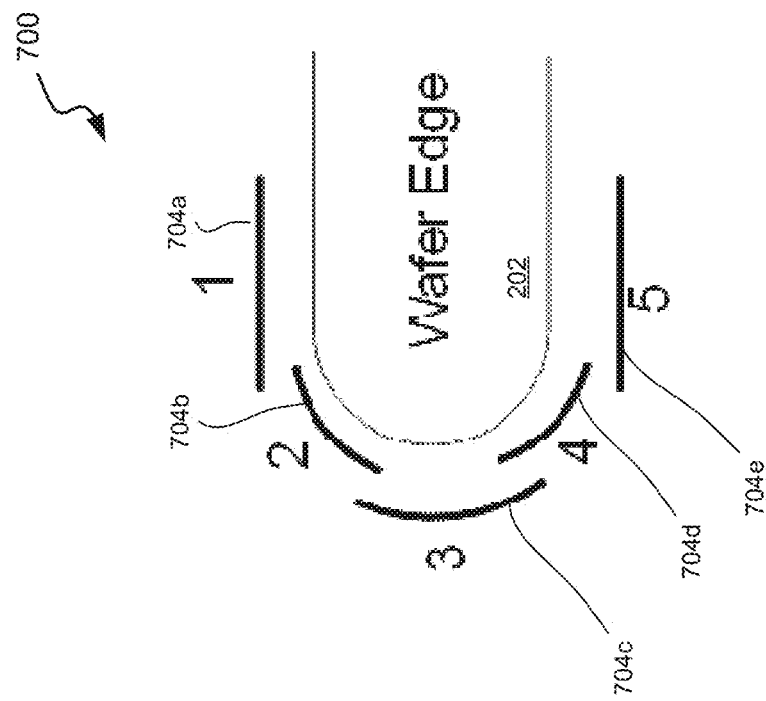
FIGS. 7A-7B illustrate an edge detection system 700 with multiple offset cameras in accordance with an alternative embodiment of the present invention.
Figure 7A:
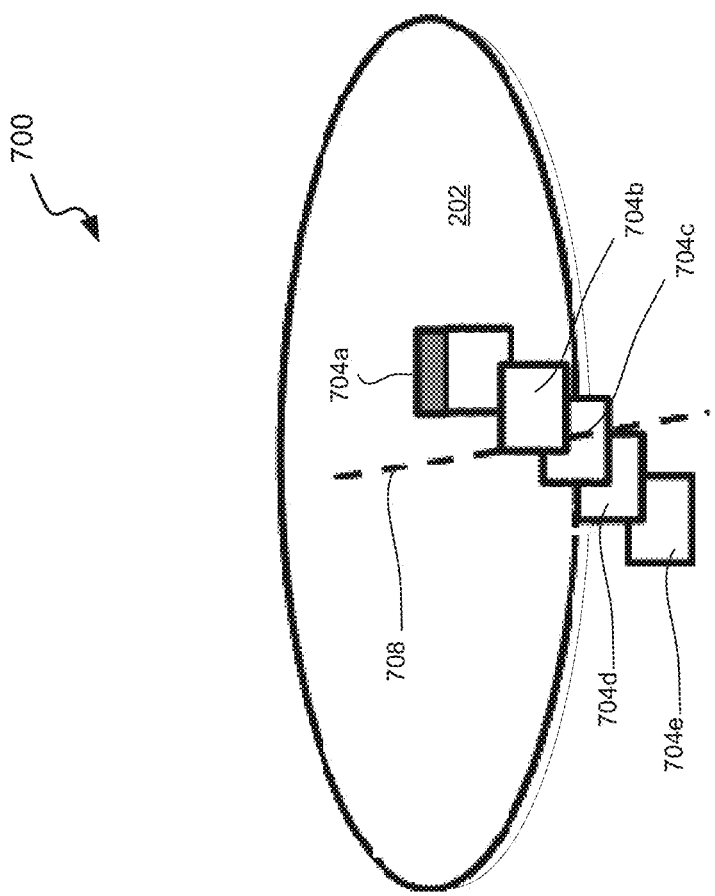

In another system configuration (e.g., reconfiguration of the WER system), multiple cameras are offset in the circumferential direction of the wafer edge to allow for the edges of the fields-of-view of the cameras to be overlapped. FIGS. 7A-7B illustrate an edge detection system 700 with multiple offset cameras 704a~704e in accordance with an alternative embodiment of the present invention. FIG. 7A is an end view, looking towards the edge-of-interest, while FIG. 7B is a side view. In this example, the cameras 704a~704e are offset from line 708. In this embodiment, a single rotation of the wafer can be sufficient to inspect the entire area of interest.

Figure 8:
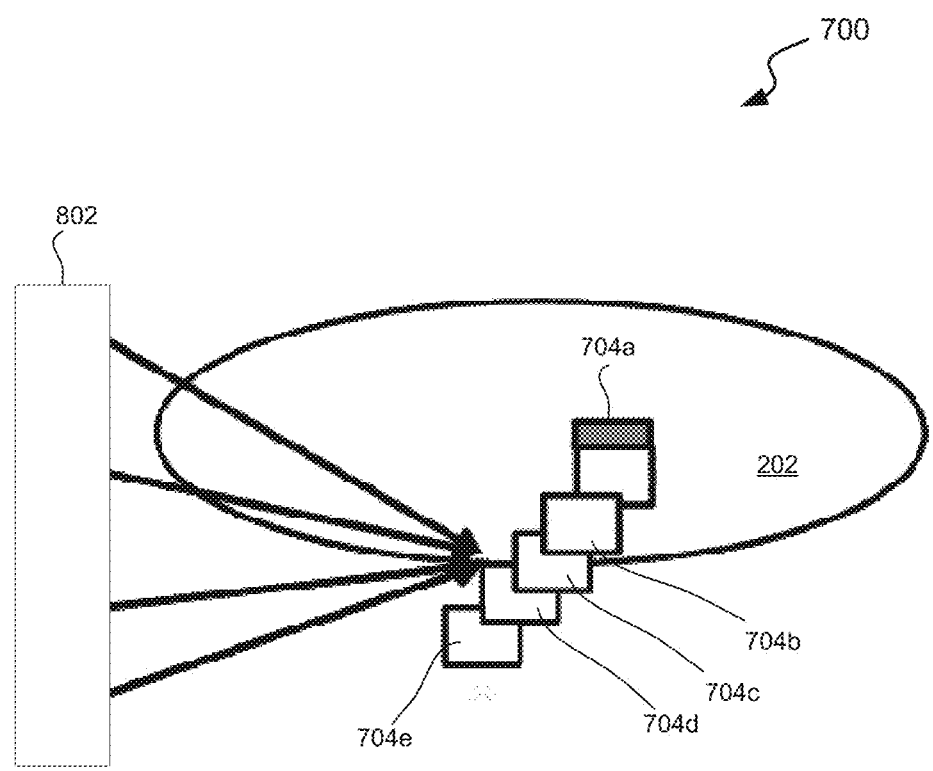
FIG. 8 illustrates an edge detection system having darkfield illumination and a plurality of cameras in accordance an example embodiment.

In general, brightfield (BF) and/or darkfield (DF) illumination mode may be provided in the above-described embodiments. For instance, the illumination may originate from within the same field of view as the cameras 704a~704e in a BF illumination mode. Alternatively, the illumination may originate from outside the field of view of the cameras in a DF illumination mode. In another example, FIG. 8 illustrates an edge detection system having darkfield illuminator 802 and a plurality of offset cameras 704a~704e in accordance an example embodiment.

Figure 9:
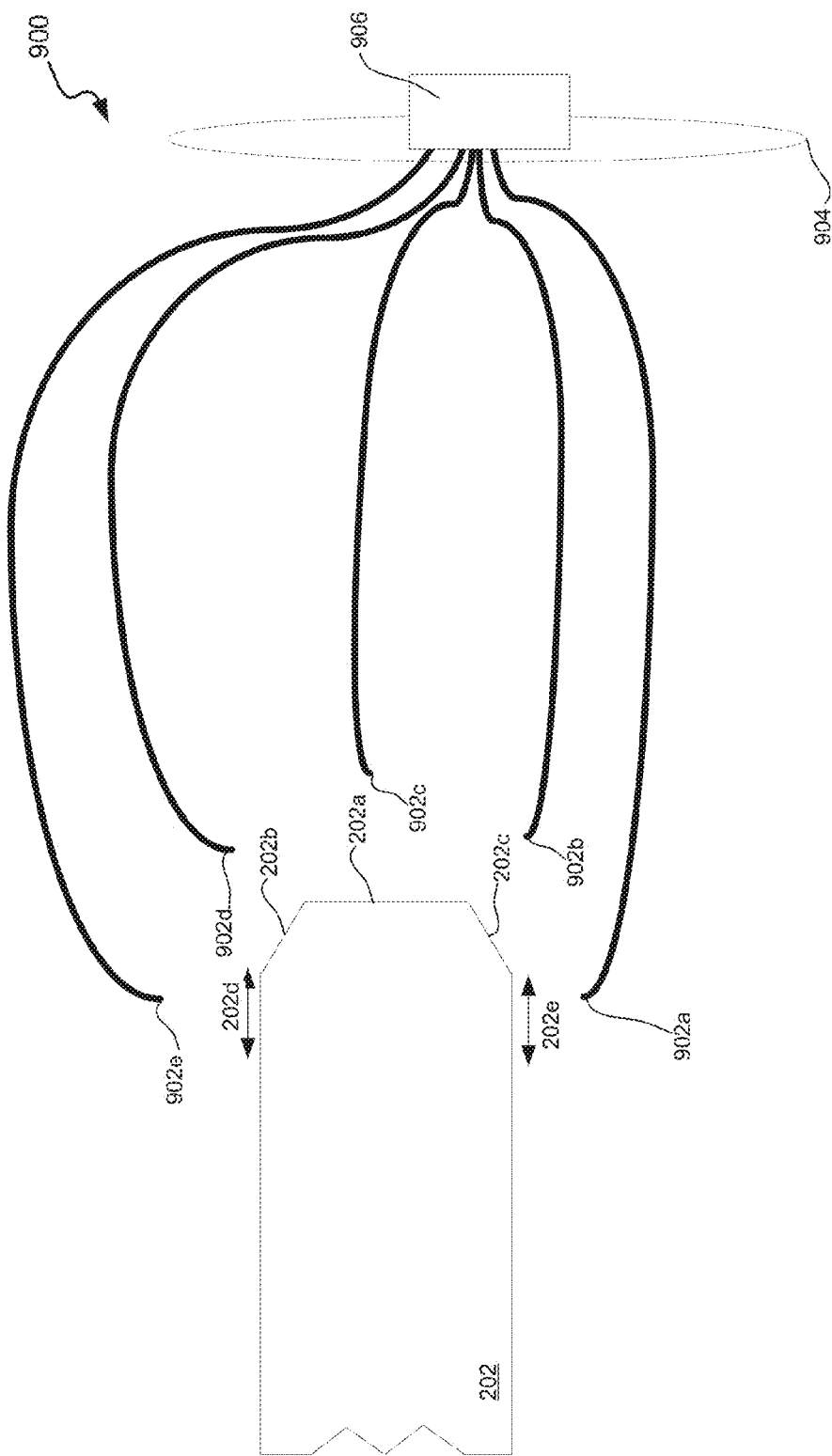
FIG. 9 illustrates another implementation that employs a coherent bundle of optical fibers in accordance with another embodiment of the present invention.

FIG. 9 illustrates another implementation that employs a coherent bundle of optical fibers in accordance with another embodiment of the present invention. The fibers include first ends 902a~902e that are positioned to approximately follow the shape of a nominal wafer edge profile, which includes surfaces 202a~e. Although the illustrated fibers only include a single fiber per sample surface, multiple fibers can be positioned above each surface. The wafer edge face could then be imaged onto the fiber bundle, and the other end 904 of the fiber bundle, arranged in a linear, flat configuration could be imaged onto a line-scan camera or TDI camera 906. Another implementation could employ optical elements to approximately map the curved surface of the wafer edge profile onto a flat sensor surface, such as a line-scan or TDI camera.

Figure 10:
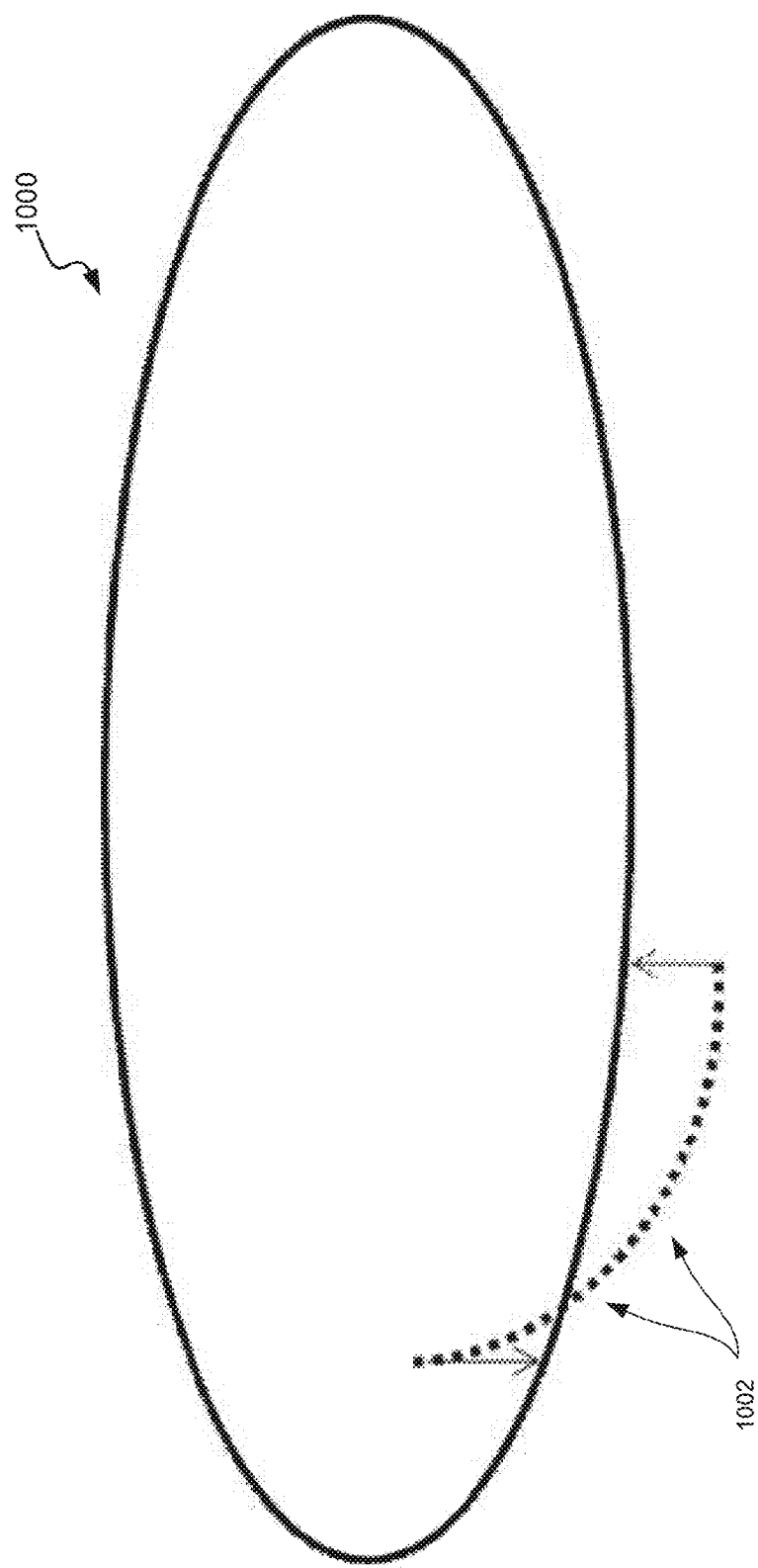
FIG. 10 is a diagrammatic representation of another edge detection system that employs multiple blue-ray illumination and sensing devices in accordance with one embodiment of the present invention.

FIG. 10 is a diagrammatic representation of another edge detection system 1000 that employs multiple illumination and sensing devices in accordance with one embodiment of the present invention. In one example, the illumination and sensing devices of a blue-ray DVD system may be implemented as a multi-spot scanning edge inspection system. The system 1000 may include a plurality of small blue-ray devices 1002 that each are configured to have a blue-violet wavelength range (e.g., 405 nm or less) with a high numerical aperture (0.85 or greater) to achieve a relative small spot size. In general, each blue ray laser device has a laser for generating an illumination light in the blue-ray wavelength range and a lens for focusing the generated illumination beam at a large numerical aperture through a small window of the device and onto the sample. Each laser device also receives light reflected (or scattered) from the sample back through the small window, and such received light is sensed by a sensor, such as a photodiode sensor, to then generate a detected signal that is output from the laser device.

These laser devices can be arranged around the edge profile to provide illumination substantially over all rounded edges of the sample, as well as the top and bottom surface portions. For example, blue ray devices are mounted onto a structure that follows the edge profile of the sample, including top and bottom border edge portions. The laser devices may be staggered with respect to each other so as to fit more laser devices along the edge profile so as to require less stepping in direction θ to fill in the spaces between the lasers in order to inspect the entire edge profile. A plurality of sensors or cameras may also be arranged around the edge profile to quickly detect scattered or reflected light from all edge surfaces, including the top and bottom border surface portions as described above. Example sensors may include any of the above-described sensors or cameras.

The edge detection systems and methods described herein may be integrated into any suitable optical imaging and inspection systems. Each edge detection system may generally include one or more light sources that each produce a light beam that is directed through illumination optics onto a sample edge. Examples of light sources include a coherent laser light source (e.g., deep UV or gas laser generator), a filtered lamp, LED light source, etc.

The image or light that is reflected and/or scattered from the sample may be directed through or reflected from a collection of optical elements to be received on one or more sensors. Suitable sensors include charged coupled devices (CCD), CCD arrays, time delay integration (TDI) sensors, TDI sensor arrays, photomultiplier tubes (PMT), and other sensors.

The signals captured by each sensor of the edge detection system 100) can be processed by a controller or analyzer computer system (e.g., 273 of FIG. 2C) or, more generally, by a signal processing device, which may include an analog-to-digital converter configured to convert analog signals from the sensors into digital signals for processing. The computer system 273 may be configured to analyze intensity, phase, images and/or other characteristics of a sensed light beam. The computer system 273 may be configured (e.g., with programming instructions) to provide a user interface (e.g., on a computer screen) for displaying images and other inspection characteristics. The computer system 273 may also include one or more input devices (e.g., a keyboard, mouse, joystick) for providing user input, such as changing detection threshold, focus, etc. In certain embodiments, the computer system 273 is configured to carry out inspection techniques detailed below. The computer system 273 typically has one or more processors coupled to input/output ports, and one or more memories via appropriate buses or other communication mechanisms.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

In certain embodiments, a system for inspecting a sample edge includes at least one memory and at least one processor that are configured to perform the above described techniques and/or to operate the edge detection tool.

It should be noted that the above diagrams and description are not to be construed as a limitation on the specific components of the system and that the system may be embodied in many other forms. For example, it is contemplated that the inspection or measurement tool may be any of a number of suitable and known imaging or metrology tools arranged for resolving the critical aspects of features of a reticle or wafer. By way of example, an inspection or measurement tool may be adapted for bright field imaging microscopy, darkfield imaging microscopy, full sky imaging microscopy, phase contrast microscopy, polarization contrast microscopy, and coherence probe microscopy. It is also contemplated that single and multiple image methods may be used in order to capture images of the target. These methods include, for example, single grab, double grab, single grab coherence probe microscopy (CPM) and double grab CPM methods. Non-imaging optical methods, such as scatterometry, may be contemplated.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. A system for inspecting and processing semiconductor wafers, the system comprising:
    an edge detection system for receiving each wafer that is to undergo a photolithography process in a photolithography system prior to the photolithography process being performed on such wafer, wherein the edge detection system comprises:
        at least one illumination channel for directing one or more illumination beams towards an edge portion of the wafer, wherein such edge portion includes at least one side, a top, and a bottom that are within a border region of the wafer,
        at least one collection module for collecting and sensing output radiation that is scattered or reflected from the edge portion of the wafer in response to the one or more illumination beams, and
        an analyzer module for locating defects in the edge portion and determining whether each wafer is within specification based on the sensed output radiation for such wafer, wherein the defects comprise particles, cracks, or scratches; and
    a photolithography system for receiving from the edge detection system each wafer that has been found to be within specification,
    wherein the edge detection system is coupled in-line with the photolithography system,
    wherein the analyzer of the edge detection system is further configured to determine an alignment position of each wafer based on the output radiation collected and sensed by the at least one collection module and such analyzer is further configured to provide such alignment position to the photolithography system, and
    wherein the lithography system is further operable to receive the alignment position of each wafer from the edge detection system and use such received alignment position to align a reticle with respect to each wafer.

2. The system of claim 1, wherein the analyzer module of the edge detection system is further configured to track the alignment position of each wafer as such wafer moves from the edge detection system to the photolithography system for alignment of such wafer during the photolithography process.

3. The system of claim 1, wherein the edge detection system is arranged to receive each wafer immediately prior to such wafer being processed by the photolithography system.

4. The system of claim 1, wherein the at least one illumination channel includes a diffractive optical element for generating a plurality of illumination beams that are directed simultaneously onto the edge portion.

5. The system of claim 4, wherein the edge detection system further includes at least one positioning mechanism for rotating each wafer under the illumination channel so that the plurality of illumination beams are scanned over the entire circumference of the edge portion of such wafer and for rotating the edge detection system over the top, bottom, and at least one side of the edge portion.

6. The system of claim 1, wherein the at least one collection module includes a darkfield channel for receiving output radiation scattered from each wafer and a brightfield channel for receiving output radiation reflected from each wafer.

7. The system of claim 1, wherein the at least one illumination channel includes a deflector mechanism for scanning the at least one illumination beam across the edge portion of each wafer.

8. The system of claim 1, wherein the at least one illumination channel and at least one collection channel are in the form of an edge inspector for inspecting the at least one side of the edge portion of each water and a top camera and a bottom camera for inspecting the top and bottom, respectively, of the edge portion of each wafer simultaneously during inspection of the at least one side.

9. The system of claim 1, wherein the at least one illumination channel and at least one collection channel are in the form of a plurality of cameras configured to simultaneously inspect the at least one side, top, and bottom of the edge portion of each wafer.

10. The system of claim 9, wherein the cameras are arranged to be offset from each other along the at least one side, top, and bottom of the edge portion of each wafer.

11. The system of claim 1, wherein the at least one illumination channel and at least one collection channel of the edge detection system comprises:
    a curved diffuser having an internal surface for positioning towards the edge portion of each wafer and an external surface opposite the internal surface;
    a plurality of light sources for generating a plurality of illumination beams adjacent to a plurality of positions on the external surface of the diffuser so that the diffuser outputs uniform light over the edge portion of each sample at a plurality of incident angles; and
    a sensor for receiving output radiation scattered from the edge portion of each wafer in response to the incident light and generating a detected signal,
    wherein the light sources, diffuser, and sensor are integrated into a compact format.

12. The system of claim 1, wherein the illumination channel is configured to provide bright field illumination and dark field illumination.

13. The system of claim 1, wherein the at least one collection channel is in the form of a fiber bundle having a plurality of first ends positioned so as to receive the output radiation from the at least one side, top; and bottom of the edge portion and a plurality of second opposite ends to output the received output radiation into a line-scan camera or time delay integration (TDI) camera.

14. The system of claim 1, wherein the at least one collection channel is in the form of a plurality of optical elements positioned so as to receive and direct the output radiation simultaneously from the at least one side, top, and bottom of the edge portion into a line-scan camera or time delay integration (TDI) camera.

15. The system of claim 1, wherein the at least one illumination channel and at least one collection channel of the edge detection system comprises a plurality of blue-ray devices arranged over the edge portion of each wafer.

16. A method of inspecting an edge portion of wafers which are undergo a photolithography process in a photolithography system, the method comprising:
for each wafer that is to undergo a photolithography process in the photolithography system, receiving the wafer into an edge detection system prior to the photolithography process being performed on such wafer;
by the edge detection system, inspecting an edge portion of each wafer for defects to determine whether the wafer is within specification, wherein such edge portion includes at least one side, a top, and a bottom that are within a border region of the wafer, wherein the defects comprises particles, cracks, or scratches;
by the edge detection system, determining an alignment position of each wafer based on the output radiation collected and sensed by a collection module of the edge detection system and providing the alignment position to the photolithography system;
for each wafer that the edge detection system determines to be within specification, outputting the wafer from the edge detection system to the photolithography system; and
by the photolithograph system, receiving the alignment position of each wafer from the edge detection system and using such received alignment position to align a reticle with respect to each wafer,
wherein the edge detection system is in-line with the photolithography system.

17. The method of claim 16, further comprising tracking defects of a particular wafer that are found to be within specification during or after such particular wafer undergoes a photolithography process.

18. The method of claim 16, wherein the edge detection system inspects wafers at a rate that is equal to or faster than a processing rate of the lithography system.

19. The method of claim 16, wherein the edge portion of each wafer is inspected with a plurality of simultaneous scanning spots that are rotated around the circumference of the wafer and stepped across the entire top and bottom and at least one side of the edge portion of the wafer.

20. The method of claim 16, further comprising:
by the edge detection system, tracking the alignment position of each water as such wafer moves from the edge detection system to the photolithography system, which uses the received alignment positions for alignment of such wafer during the photolithography process.

21. The method of claim 20, further comprising:
cleaning each wafer that is determined to be out of specification and to be cleanable prior to sending the wafer to the photolithography system,
wherein the cleaning is performed in an internal cleaning system that is in-line with the edge detection and photolithography system.

* * * * *

UNITED STATES PATENT AND TRADEMARK OFFICE
CERTIFICATE OF CORRECTION

PATENT NO. : 9,645,097 B2  
APPLICATION NO. : 14/741866  
DATED : May 9, 2017  
INVENTOR(S) : Lena Nicolaides et al.

It is certified that error appears in the above-identified patent and that said Letters Patent is hereby corrected as shown below:

In the Claims

In Column 19, Line 13, Claim 16, please amend as follows:
"A method of inspecting an edge portion of wafers which are to undergo a photolithography process in a photolithography system, the method comprising:"

Signed and Sealed this
First Day of August, 2017

Joseph Matal
*Performing the Functions and Duties of the*
*Under Secretary of Commerce for Intellectual Property and*
*Director of the United States Patent and Trademark Office*